United States Patent [19]

Beutler et al.

[11] Patent Number: 5,447,851
[45] Date of Patent: Sep. 5, 1995

[54] DNA ENCODING A CHIMERIC POLYPEPTIDE COMPRISING THE EXTRACELLULAR DOMAIN OF TNF RECEPTOR FUSED TO IGG, VECTORS, AND HOST CELLS

[75] Inventors: Bruce A. Beutler; Karsten Peppel, both of Dallas; David F. Crawford, Irving, all of Tex.

[73] Assignee: Board of Regents, The University of Texas System, Austin, Tex.

[21] Appl. No.: 862,495

[22] Filed: Apr. 2, 1992

[51] Int. Cl.$^6$ .................. C12P 21/06; C12N 15/00; C07H 17/00; C07K 14/00
[52] U.S. Cl. ................... 435/69.7; 435/69.5; 435/240.2; 435/320.1; 536/23.4; 530/300; 530/351
[58] Field of Search ............. 435/69.5, 69.7, 320.1; 530/351; 536/23.4, 23.51

[56] References Cited

U.S. PATENT DOCUMENTS

| | | | |
|---|---|---|---|
| 4,894,439 | 1/1990 | Dorin et al. | 530/351 |
| 5,055,447 | 10/1991 | Palladino et al. | 514/12 |
| 5,155,027 | 10/1992 | Sledziewski | 435/69.7 |

OTHER PUBLICATIONS

Askenazi et al. (1991) PNAS 88 10535–10539.
Gray et al. 1990 PNAS 87:7380–7384.
Dimmler et al. 1990 DNA & Cell Biol. 9(10):705–715.
Sombrook et al. 1989 Molecular Cloning: A Lab. Manual. CSHL Press, Cold Spring Harbor, N.Y.
Smith et al. 1989 J. Biol. Chem. 264(25):14646–14852.
Loetscher et al. 1991 J. Biol. Chem. 266(27):18324–18329.
Ashkenazi et al.; "Protection against endotoxic shock by a tumor necrosis factor receptor immunoadhesin"; Proc. Natl. Acad. Sci. USA; vol. 88, pp. 10535–15039; Dec. 1991.
Fomegaard et al.; "Preliminary Study on Treatment of Septic Shock Patients with Antilipopolysaccharide IgG from Blood Donors"; Scand J Infect Dis 21 (1989).
Lesslauer et al.; "Recombinant soluble tumor necrosis factor receptor proteins protect mice from lipopolysaccharide-induced lethality"; Eur. J. Immunol. 1991.21: 2883–2886.
Romagnani et al.; "New Advances on Cytokines"; Structural and Functional Analysis of a TNF Receptor–Immunoglobulin Fusion Protein; vol. 92 pp. 349–354.
Traunecker et al., "Highly Efficient Neutralization of HIV with Recombinant CD4–Immunoglobulin Molecules," Nature 339:68–70 (1989).
Lostacher et al., "Molecular Cloning and Expression of the Human 55 kD Tumor Necrosis Factor Receptor," Cell 61:351–359 (1990).

(List continued on next page.)

Primary Examiner—Garnette D. Draper
Assistant Examiner—K. Cochrane Carlson
Attorney, Agent, or Firm—Arnold, White & Durkee

[57] ABSTRACT

The invention relates generally to DNA sequences encoding chimeric polypeptides comprising extracellular portions of cytokine receptor polypeptides attached to a sequence encoding portions of IgG polypeptides. The invention relates generally, as well, to DNA sequences encoding chimeric polypeptides comprising extracellular portions of cytokine receptor polypeptides attached through oligomers encoding specifically cleavable peptide linkers to a sequence encoding portions of IgG heavy chain polypeptides More specifically, the invention relates to a construction in which a cDNA sequence encoding the extracellular domain of the human 55 kD TNF receptor is attached through an oligomer encoding a thrombin-sensitive peptide linker to a sequence encoding the $F_c$ portion and hinge region of a mouse IgG1 heavy chain. The invention relates as well to uses of the chimeric polypeptide, including: use as a reagent for the antagonism and assay of TNF and lymphotoxin from diverse species; use as a means of determining the mechanism by which TNF, or analogs thereof, interacts with the TNF receptor; use as an antitumor reagent, particularly against placental tumors; and, use as a reagent capable of controlling birth.

25 Claims, 9 Drawing Sheets

OTHER PUBLICATIONS

Smith et al., "A Receptor for Tumor Necrosis Factor Defines an Unusual Family of Cellular and Viral Proteins," *Reports,* pp. 1019–1023 (May 25, 1990).

Schall et al., "Molecular Cloning and Expression of a Receptor for Human Tumor Necrosis Factor," *Cell* 61:361–370 (1990).

Engelmann et al., "A Tumor Necrosis Factor-Binding Protein Purified to Homogeneity from Human Urine Protects Cells from Tumor Necrosis Factor Toxicity," *Jour. Biol. Chem.* 264:11974–11980 (1989).

Liabakk et al., "A Rapid and Sensitive Immunoassay for Tumor Necrosis Factor Using Magnetic Monodisperse Polymer Particles," *Jour. Immunol. Methods* 134:253–259 (1990).

Peppel et al., "A Tumor Necrosis Factor (TNF) REceptor–IgG Heavy Chain Chimeric Protein as a Bivalent Antagonist of TNF Activity," *J. Exp. Med.,* 174:1483–1489, 1991.

Dialog Search Report dated Feb. 26, 1991.

DNA ENCODING A CHIMERIC POLYPEPTIDE COMPRISING THE EXTRACELLULAR DOMAIN OF TNF RECEPTOR FUSED TO IGG, VECTORS, AND HOST CELLS

BACKGROUND OF THE INVENTION

This invention was made with government support under grant no. P01-DK42582-01 awarded by the National Institutes of Health. The government may have certain rights in the invention.

A. Field of the Invention

The invention relates generally to DNA sequences encoding chimeric polypeptides comprising extracellular portions of cytokine receptor polypeptides attached to a sequence encoding portions of IgG polypeptides. In another embodiment, the invention relates generally to DNA sequences encoding chimeric polypeptides comprising extracellular portions of cytokine receptor polypeptides attached through oligomers encoding specifically cleavable peptide linkers to a sequence encoding portions of IgG polypeptides. More specifically, the invention relates to a construction in which a cDNA sequence encoding the extracellular domain of the human 55 kD TNF receptor is attached through an oligomer encoding a thrombin-sensitive peptide linker to a sequence encoding the $F_c$ portion and hinge region of a mouse IgG1 heavy chain polypeptide. In certain aspects, this construct is placed downstream from a cytomegalovirus promoter sequence, expressed in a host cell such as Chinese hamster ovary cells, and the chimeric polypeptide is recovered. In other embodiments, the chimeric polypeptide is expressed in insect cells using a baculovirus promoter. The invention relates as well to uses of the chimeric polypeptide. Methods are disclosed relying on the inhibitory activity of the chimeric polypeptide including: use as a reagent for the antagonism and assay of TNF and lymphotoxin from diverse species; use as a means of determining the mechanism by which TNF, or analogs thereof, interacts with the TNF receptor; use as an antitumor reagent, particularly against placental tumors as well as other tumors that secrete TNF; and, use as a reagent capable of controlling birth.

B. Description of the Related Art

TUMOR NECROSIS FACTOR

Tumor necrosis factor-alpha (TNF-alpha; or TNF) is a protein essential as a mediator of the inflammatory response. TNF-alpha is identical to the hormone cachectin and is an important endogenous factor in the pathogenesis of chronic wasting associated with acute inflammatory or malignant diseases (Beutler and Cerami 1988).

TNF possess an antitumor activity, causing hemorrhagic necrosis in tumors in mice treated with BCG and endotoxin. TNF-alpha is the major mediator of endotoxin shock, a disease in which hypotension, derangement of lipid and glucose metabolism, acidosis, and widespread neutrophil activation can lead to increased catabolic metabolism and potentially to death.

TNF is involved in other disease states, as well. Cachexia, (anorexia and wasting in chronic infectious or malignant disease) is also evoked by TNF-alpha partially through suppression of the enzyme lipoprotein lipase and by mobilization of triglycerides in adipocytes, and partly through induction of anorexia. Through complex effects on endothelial and neutrophil cells, TNF-alpha also causes neutrophils to adhere to lung capillaries enhancing thrombus formation. This may result variously in disseminated intravascular coagulation, migratory thromboses and hemorrhagic necroses. TNF-alpha is also a potent endogenous pyrogen affecting hypothalmic neurons and promoting IL-1 production. TNF has also been implicated in the pathogenesis of malaria and gram-negative septic shock.

The role of TNF in non-disease states has also been investigated. For instance, Eades et al. (1988) characterized a TNF receptor in human placenta. In fact, it has been shown that human placental tissue secretes TNF (Jäättelä et al. 1988).

TNF-alpha monomer itself is a polypeptide of 17 kD consisting of 150-160 amino acids (Beutler and Cerami 1986). The protein is isolatable from the supernatant of stimulated human macrophages, or, in highly purified form, as a recombinant protein (Shirai et al. 1985). The bioactivity of TNF-alpha is nearly indistinguishable from that of the cytotoxic polypeptide hormone lymphotoxin, produced by activated lymphocytes (also identified as TNF-beta). The two molecules are structurally related, being encoded by closely linked genes within the major histocompatibility complex. As a result, the two proteins share common receptors on a large variety of cells. Both lymphotoxin (TNF-beta) and TNF-alpha are bound by a 55 kD receptor with comparable affinity (Loetscher et al. 1990; Schall et al. 1990; Dembic et al. 1990; Kobno et al. 1990; Smith 1990). For purposes of the current application, TNF may be used interchangeably to indicate either TNF-alpha or TNF-beta.

TNF-alpha is produced by all types of macrophages in a degree dependent on the maturation and differentiation state, as well as by T lymphocytes in response to a variety of invasive stimuli. The most potent known stimulus is the bacterial lipopolysaccharide (LPS). Viruses, trypanosoma, plasmodium, some Gram-positive bacteria, and the cytokine IL-1 also stimulate TNF-alpha production (Beutler and Cerami 1986).

TNF-alpha is, however, subject to rapid clearance in vivo and this is likely to result in lower measured TNF values in immunoassays. TNF-alpha dissociates and aggregates to yield a protein of variable size. The biologically active form of TNF-alpha is believed to be a dimeric or trimeric species (Smith and Baglioni 1989). Dissociation of the trimeric protein is believed to be responsible for the instability of biologically active TNF-alpha in dilute solutions (Smith and Baglioni 1989). Failure to detect TNF-alpha activity in stored sera has also been reported.

IMMUNOASSAYS FOR TUMOR NECROSIS FACTOR

Immunoassays for TNF-alpha have been described in the literature. For example, EPO Published Application 218,868 discloses the preparation of pure human tumor necrosis factor. The application further discloses hybridomas which produce monoclonal antibodies to human tumor necrosis factor and use of the monoclonal antibodies for diagnostic purposes. JP Published Application 60208924 discloses a monoclonal antibody to human tumor necrosis factor and its use in immunoassays. Current methods that measure TNF-alpha concentrations in biological samples (e.g., immunometric or immunoprecipitation assays) measure total TNF, and do not give an indication of the quantity of active TNF present in vivo.

The sensitivity of a radioimmunoassay is generally limited by ligand affinity. Antibodies typically exhibit combining group affinities in the range of $10^5$ to $10^6$ Ka. Certain prior approaches have attempted to utilize antibodies to detect TNF in biological samples. Liabakk et al. (1990), for instance, relates to an immunoassay for TNF using monoclonal antibody capable of detecting 62 to 4,000 pg/ml of TNF. PCT Patent WO 90/06514 relates to an "sandwich" immunometric assay for detecting biologically active TNF and a method for blocking degradation of TNF in a biological sample. Since the assay uses two antibodies competing for the same epitope on the TNF molecule, it is stated to discriminate between the inactive and active forms of human TNF-alpha by virtue of the fact that active TNF exists as a dimer or trimer only. Japanese Patent 63,253,099 relates to a monoclonal antibody said to be specific to the active site of human TNF and which does not bind inactive human TNF.

However, the sensitivity of a radioimmunoassay is generally limited by ligand affinity. The affinity of the interaction between TNF and the combining site of soluble TNF receptors has been estimated by several laboratories, and assigned a Ka value in a range between $10^9$ and $10^{10}$ (Engelmann et al. 1989; Sackinger et al. 1989; Beutler et al. 1985; Smith et al. 1986).

TUMOR NECROSIS FACTOR RECEPTORS

The cloning of the 55 kD (Loetscher et al. 1990; Schall et al. 1990; Dembic et al. 1990) and 75 kD (Dembic et al. 1990; Kobno et al. 1990; Smith 1990) TNF receptors has opened the way for further studies of TNF effects and signal transduction. Moreover, it would appear that truncated receptor molecules, lacking the transmembrane or cytoplasmic domains, are capable of interacting with TNF, and therefore, have been isolated from urine (Engelmann et al. 1989; Sackinger et al. 1989) and serum (Schall et al. 1990) as "TNF inhibitors."

Unfortunately, truncated forms of the TNF receptor are highly unstable in vivo. Therefore, naturally isolated truncated forms are poor substitutes for antibodies as a means of antagonizing TNF action in living animals. Naturally occurring TNF receptor fragments are univalent and therefore, have an avidity that is effectively far lower than that of a bivalent ligand.

The production of large quantities of eukaryotic proteins such as a truncated receptor polypeptide by recombinant means are not uncommonly problematic, since the protein is produced in an inactive and insoluble form in bacteria. This difficulty may arise from highly cysteine-rich structures typical of the receptor binding domains as can be found in the TNF receptor polypeptides (Loetscher et al. 1990; Schall et al. 1990). Even when produced in mammalian cells through recombinant techniques, the soluble receptor fragments, although active, may be produced at low levels and may be difficult to purify.

One approach to overcoming certain of the problems typically encountered in expressing eukaryotic receptor proteins in high levels may be seen in the work of Capon et al. (1989), and Traunecker et al. (1989). These workers designed secreted chimeric molecules in which the binding moiety of a CD4 molecule was adjoined to an IgG heavy chain. This molecule circulated for a prolonged period of time in vivo. Thus, the use of IgG heavy chain as a partner in chimeric molecules may comprise a generally useful strategy for the expression of molecules that would otherwise prove unstable in circulation.

Other chimeric proteins have been produced to overcome substantial problems with expression (see, e.g., PCT Patent WO 90/12877). For instance, a recombinant 55 kD TNF receptor polypeptide chimera representing the extra-cellular domain of the receptor has been expressed as a secreted protein in baculovirus-infected insect cells and Chinese hamster ovary cells as a fusion with the hinge region of human IgG expressed in mouse myeloma cells (Loetscher 1991).

Engelmann et. al. (1990) demonstrated that polyclonal antiserum raised against soluble TNF receptors can mimic the cytotoxic activity of TNF in the presence of cycloheximide and can also reproduce a variety of other responses ascribed to TNF. These workers were able to show that crosslinking of TNF receptors on the cell surface by antibodies was both necessary and sufficient to induce lysis in sensitive target cells. This led these workers to propose that crosslinking of TNF receptors by TNF is the primary mode of signal transduction. Smith and Baglioni have shown the trimer to be the active form of TNF (1989). Mutagenesis studies have shown the subunit interface to be involved in receptor binding (1991).

CERTAIN PROBLEMS REMAINING IN PRIOR ART APPROACHES

Reagents are needed which are capable of selectively detecting active TNF molecules (harmful) rather than both active and inactive (i.e., molecules bound to serum inhibitors, or molecules that have been partially degraded; and, thus, not harmful). Such molecules will preferably be additionally capable of detecting TNF produced in more than a single species (human). In addition, it would be preferable if such reagents bind TNF with higher affinity than do antibodies directed toward the necrosis factor. Most preferably, such reagents will bind only with the active fraction of TNF. Particular utility would be attributable to reagents that will also bind to all TNFs including lymphotoxins. Reagents such as these may provide novel approaches to disease treatment and diagnosis related to TNF.

SUMMARY OF THE INVENTION

In order to overcome at least some of the limitations of the prior art, the present invention discloses a chimeric protein in which the extracellular domain of a cytokine receptor, which normally engages the cytokine molecule, is covalently linked to an IgG molecule. In particular, and by way of example, a TNF receptor extracellular polypeptide is coupled to the $CH_2$ through $CH_3$ regions of a mouse IgG1 heavy chain. Interposed between the two polypeptide sequences is a peptide susceptible to cleavage by a specific protease or other peptide cleaving reagent. In a particular embodiment, a hexapeptide sensitive to cleavage by thrombin is used. The chimeric protein is expressed and secreted by CHO cells. In another embodiment, the insect cell lines SF9 and SF21 may be used in combination with a baculovirus promotor hooked up to the chimeric polypeptide. Whichever vector/host system is utilized, the resulting recombinant chimera is highly active as a TNF inhibitor, is readily purified by affinity chromatography using an anti-mouse IgG or Protein A column, and is quantitatively cleaved by thrombin to yield the extracellular domain in an active form.

In particular, the reagents of the present invention are capable of selectively detecting active TNF molecules rather than both active and inactive TNF. Such molecules are additionally capable of detecting TNF produced in many species, including humans. In addition, the reagents of the invention bind TNF with higher affinity than do antibodies directed toward the necrosis factor. A particular advantage of the present invention is the production of reagents that will bind only with the active fraction of TNF. Particular utility is ascribed to the invention reagents since they also bind to TNFs including lymphotoxins. As such, derivatives of such molecules might prove useful as antagonists of TNF action in vivo, as high affinity ligands to be applied as the basis of a more sensitive assay for TNF, and as reagents to be utilized in defining the molecular interaction between TNF and its receptor.

VECTORS

In one of its most general applications, the invention relates to a recombinant vector incorporating a DNA segment having a sequence encoding a chimeric polypeptide. The chimeric polypeptide is constructed by coupling an extracellular portion of a cytokine receptor polypeptide to an IgG heavy chain polypeptide. For the purposes of the invention, the term chimeric polypeptide is defined as including any polypeptide where at least a portion of a cytokine receptor polypeptide is coupled to at least a portion of an IgG heavy chain polypeptide. The coupling is achieved in a manner which provides for a functional transcribing and translating of the DNA segment and message derived therefrom, respectively. Where such a receptor has two polypeptide chains, the DNA segment encoding the second polypeptide chain may be functionally coupled to a DNA segment encoding an IgG light chain polypeptide in a manner to produce a receptor-IgG light chain chimeric molecule.

The cytokine receptor polypeptides of the invention may be any of a number of such receptors known in the art. A list of certain of these receptors is provided below (specifically incorporated by reference herein to the extent that the reference includes methodology providing access to such receptors). Generally, such a receptor polypeptide will be one in which there is a known extracellular domain and which polypeptide has had the DNA sequence encoding it isolated.

CYTOKINE RECEPTORS

Human intercellular adhesion molecule (ICAM-1)
Stauton et al., *Cell* 52:925–953 (1988).
Human interferon gamma receptor
Aguet et al., *Cell* 55:273–280 (1988)
Human interferon alpha receptor
Uze et al., *Cell* 60:225–234 (1990)
Human Mac-1 (human complement receptor type 3)
Corbi et al., *J. Biol Chem.* 263:12403–12411 (1988)
Human insulin receptor
Ebina et al., *Cell* 40:747–758 (1985)
Human transferrin receptor
McClelland et al., *Cell* 39:267–274 (1984)
Human nerve growth factor receptor
Johnson et al., *Cell* 47:545–554 (1986)
Human leukocyte adhesion protein (beta subunit)
Kishimoto et al., *Cell* 48:681–690 (1987)
Human leukocyte adhesion receptor (alpha subunit)

Arnaout et al., *J. Biol. Chem.* 106:2153–2158 (1988)
Human interleukin-6 receptor
Yamasaki et al., *Science* 241:825–828 (1988)
Human platelet-derived growth factor (PDGF) receptor
Claesson-Welsh et al., *Molec. Cell. Bio.* 8:3476–3486 (1988)
Human insulin-like growth factor receptor
Ullrich et al., *EMBO J.* 5:2503–2512 (1986)
Human interleukin-2 receptor (beta chain), pp. 70–75

Hatakeyama et al., *Science* 244:551–556 (1989)
Human interleukin-1 receptor
Sims et al., *Proc. Ntl. Acad. Sci. USA* 86:8946–8950 (1989)
Human epidermal growth factor receptor
Kraus et al., *Proc. Ntl. Acad. Sci. USA* 86:9193–9197 (1989)
Human leukocyte adhesion protein, pp. 150, 95 (alpha subunit)
Corbi et al., *EMBO J.* 6:4023–4028 (1987)
Human interleukin-7 receptor
Goodwin et al., *Cell* 60:941–951 (1990)
Human vascular cell adhesion molecule-1
Osborn et al., *Cell* 59:1203–1211 (1989)
Human endothelial leukocyte adhesion molecule-1 (elam-1)
Hession et al., *Proc. Ntl. Acad. Sci. USA* 87:1673–1677 (1990)
Human prolactin receptor
Boutin et al., *Mol. Endocrinol.* 3:1455–1461 (1989)
Human thyrotropin receptor
Nagayama et al., *Biochem. Biophys. Res. Comm.* 165:1184–1190 (1989)
Human leukocyte adhesion molecule-1 (lam-1)
Ord et al., *J. Biol. Chem.* 265:7760–7767 (1990)
Human basic fibroblast growth factor receptor (shorter form)
Itoh et al., *Biochem. Biophys. Res. Comm.* 169:680–685 (1990)
Human granulocyte-colony stimulating factor (G-CSF) receptor
Fukunaga et al., *Proc. Ntl. Acad. Sci. USA* 87:8702–8706 (1990)
Human granulocyte macrophage-colony stimulating factor (GM-CSF) receptor (beta chain)
Hayashida et al., *Proc. Ntl. Acad. Sci. USA* 87:9655–9659 (1990)
Human interleukin-2 receptor (TACT antigen or 55k subunit)
Leonard et al., *Nature* 311:626–631 (1984)
Human stem cell factor receptor (c-kit)
Yarden et al., *EMBO J.* 6:3341–3351 (1987)
Human growth hormone receptor
Leung et al., *Nature* 330:537–543 (1987)
Human intercellular adhesion molecule-2 (ICAM-2)
Staunton et al., *Nature* 399:61–64 (1989)
Human leukocyte function associated molecule-1 (LFA-1)(alpha subunit)
Larson et al., *J. Cell Biol.* 108:702–712 (1989)
Human interleukin-4 receptor
Idzerda et al., *J. Exp. Med.* 171:861–873 (1990)

Human erythropoietin receptor
Winkelmann et al., *Blood* 76:24–30 (1990)
Human Fas Antigen
Itoh et al., *Cell* 66:233–243 (1991)

The vector may further incorporate a specifically cleavable linker peptide functionally interposed between the cytokine receptor polypeptide and the IgG heavy chain polypeptide.

Such a linker peptide provides by its inclusion in the chimeric construct, a site within the resulting chimeric polypeptide which may be cleaved in a manner to separate the intact cytokine receptor polypeptide from the intact IgG heavy chain polypeptide. Such a linker peptide may be, for instance, a peptide sensitive to thrombin cleavage, factor X cleavage or other peptidase cleavage. Alternatively, where the chimeric polypeptide lacks methionine, the IgG domain may be separated by a peptide sensitive to cyanogen bromide treatment. In general, such a linker peptide will describe a site which is uniquely found within the linker peptide and is not found at any location in either of the polypeptides constituting the chimeric polypeptide. In certain embodiments of the invention, the specifically cleavable linker peptide comprises a thrombin-sensitive linker peptide.

The cytokine receptor polypeptide will be a TNF receptor polypeptide, in certain preferred embodiments. Of particular utility in human medicine, the TNF receptor polypeptide will be a human TNF receptor polypeptide. In any case, the polypeptide will represent at least a portion of the extracellular domains of the native receptor polypeptide.

In certain specific embodiments, the IgG heavy chain polypeptide will comprise an $F_c$ portion and hinge region of the IgG heavy chain polypeptide. In others, the IgG heavy chain polypeptide will be a mouse IgG polypeptide. It will be understood, however, that other portions of antibody molecules will find similar use in such chimeric constructions. For instance, it may be desirable to attach receptor domains to the light-chain of the immunoglobulin molecule. This may be particularly useful in those cases in which the active form of the receptor consists of two polypeptide chains. For instance, such a situation obtains in the case of the ILl-2 receptor, and certain other receptors as well. In such instances, one of the receptor chains is spliced to the IgG light-chain. Splicing would most commonly involve the attachment of these chains to the most N-terminal domain of the heavy and light chain subunits of the IgG molecule. The juxtaposition of the receptor extracellular domains would be arranged so as to approximate the natural union of these two molecules on the cell membrane. Since several IgG molecules have been studied at a crystallographic level, the exact point of attachment may be guided by an analysis of the spatial relationship of various amino acid residues within the heavy and light chains of the IgG molecule. In general a splice site in the constant heavy I($C_H$I) domain and a splice site in the constant light I domain would be chosen.

The vectors of the invention will generally be constructed such that the chimeric polypeptide encoding sequence is positioned adjacent to and under the control of an effective promoter. In certain cases, the promotor will comprise a prokaryotic promoter where the vector is being adapted for expression in a prokaryotic host. In other cases, the promoter will comprise a eukaryotic promoter where the vector is being adapted for expression in a eukaryotic host. In the later cases, the vector will typically further include a polyadenylation signal position 3' of the carboxy-terminal amino acid, and within a transcriptional unit of the encoded chimeric polypeptide. Promoters of particular utility in the vectors of the invention are cytomegalovirus promoters and baculovirus promoters, depending upon the cell used for expression. A number of vectors capable of use with the DNA segments of the invention and which contain a cytomegalovirus promoter are the pCMV vectors which will be discussed in greater detail below. Regardless of the exact nature of the vector's promoters, the recombinant vectors of the invention will incorporate a DNA segment as defined below.

ISOLATED DNA SEGMENTS

Isolated DNA segments are also claimed having a sequence encoding a chimeric polypeptide comprising an extracellular portion of a cytokine receptor polypeptide functionally attached to an IgG polypeptide. In other constructions enabled herein, the cytokine receptor polypeptide may be functionally attached first to a specifically cleavable linker peptide which is in turn functionally attached to an IgG polypeptide. As described supra, the isolated DNA segment of the invention may be one in which the cytokine receptor polypeptide is a TNF receptor polypeptide. The DNA segment more specifically may be a human TNF receptor polypeptide.

The isolated DNA segment of the invention may also be one in which the IgG polypeptide comprises an $F_c$ portion and hinge region of the IgG heavy chain polypeptide. In certain embodiments, the DNA segment the IgG polypeptide may be one derived from mouse. Although it is not necessary for certain embodiments, the isolated DNA segment of the invention may additionally comprise a specifically cleavable linker peptide such as a thrombin-sensitive linker peptide.

It will be understood by those of skill in the art that any isolated DNA segment having at least a 14 base sequence of a DNA sequence encoding a portion of a polypeptide comprising an extracellular portion of a cytokine receptor polypeptide functionally attached to a portion of an IgG heavy chain polypeptide will be of utility as described herein. For instance, such a construct would allow the hybridization and isolation of similar sequences amongst a collection of dissimilar sequences, such as where mutations in the original chimeric polypeptide are introduced and it is desired to select only those containing the 14 base sequence identically. In other instances, DNA segments of at least 20, 30 or 40 bases will find particular utility, since such extended DNA segments will possess even higher degrees of homology with the two polypeptide sequences it encodes and can be expected to exhibit even higher affinity for binding similar sequences.

Where the specific construction consists additionally of a specifically cleavable linker peptide functionally interposed between the two polypeptides, then the DNA segment will encode at least the linker peptide and portions of either of the two flanking polypeptides. In most instances, such a DNA segment will be encoded by at least 20 or more bases.

Regardless of its precise length, the isolated DNA segment of the invention may be one where the cytokine receptor polypeptide comprises a TNF receptor polypeptide. It may also be one where the IgG heavy chain polypeptide comprises an $F_c$ portion and hinge region of the IgG heavy chain polypeptide, and in certain other instances, a mouse IgG polypeptide. The isolated DNA segment may also be one where the specifically cleavable linker peptide comprises a thrombin-sensitive linker peptide.

CHIMERIC POLYPEPTIDES

Disclosed herein as well are chimeric polypeptides comprising an extracellular portion of a cytokine receptor polypeptide functionally attached to an IgG heavy chain polypeptide. Where such a construction is preferred, the chimeric polypeptide may additionally comprise a specifically cleavable linker peptide which is interposed between and functionally attached to both of the flanking polypeptides.

As described supra, the chimeric polypeptide may be one where the cytokine receptor polypeptide comprises a TNF receptor polypeptide. Additionally, the chimeric polypeptide may be one in which the IgG heavy chain polypeptide comprises an $F_c$ portion and hinge region of the IgG heavy chain polypeptide, in certain cases derived from mice. Where it will find utility, the chimeric polypeptide may additionally comprise a specifically cleavable linker peptide such as a thrombin-sensitive linker peptide.

RECOMBINANT HOST CELLS

A recombinant host cell is also claimed herein which incorporates an isolated DNA segment in accordance with any of the claims directed to such a DNA segment. The recombinant host cell may be either a eukaryotic cell or a prokaryotic host cell. Where a eukaryotic cell is used, a Chinese Hamster Ovary (CHO) cell is of particular utility. In a preferred embodiment, when used in combination with a baculovirus promoter, the insect cell lines SF9 or SF21 will be used. In any case, the DNA segment encoding a chimeric polypeptide is placed under the transcriptional control of regulatory signals functional in the recombinant host cell which regulatory signals appropriately control the expression of the chimeric polypeptide in a manner to allow all necessary transcriptional and post transcriptional modification.

METHODS

A method of producing a chimeric polypeptide is disclosed herein as well. That method comprises producing a recombinant host cell as described above so as to produce a recombinant host cell capable of expressing the polypeptide. Next, the host cell is cultured under conditions appropriate for expressing the polypeptide. At the end of such a culturing period, the polypeptide is recovered from these cells or from the culture fluid in which they were grown or both.

In other embodiments, the method for producing the polypeptides of the invention may comprise the additional steps of: first cleaving the polypeptide at the specifically cleavable linker peptide; and, then, recovering the cleaved polypeptide comprising an extracellular portion of a cytokine receptor polypeptide.

The method of producing the chimeric polypeptides of the invention may utilize a eukaryotic cell such as a CHO or insect cell or it may utilize a prokarotic cell. However, in order to maximize the amount of active polypeptide recovered from such cells, eukaryotic cells are preferred.

A method of producing an antibody reactive with a chimeric polypeptide invention is also disclosed. This method comprises, first, producing a recombinant host cell according to the teachings of the invention so that such a cell is capable of expressing the chimeric polypeptide and, next, culturing the host cell under conditions appropriate for expressing the chimeric polypeptide. The chimeric polypeptide is then recovered and is used to prepare an antibody to the chimeric polypeptide. In certain embodiments, the antibody may be a monoclonal antibody. In a preferred embodiment, the epitopic region of the chimeric polypeptide will comprise the juncture including the extracellular portion of a cytokine receptor polypeptide, the linker peptide, and the IgG chain. Using the antibody capable of distinguishing intact (uncleaved) chimeric polypeptide molecules from cleaved molecules, it will be possible to further purify such chimeric polypeptides.

Methods for assaying a candidate substance for its ability to interact with a cytokine receptor polypeptide are also disclosed. One first obtains a cytokine receptor polypeptide using the approach taught by the invention. After obtaining such a polypeptide in sufficient quantity and purity, one next exposes the polypeptide to a candidate substance. Finally, a variety of means are employed which allow evaluation of the interaction of the polypeptide with the candidate substance. A candidate substance may be any substance potentially capable of interacting with the cytokine receptor polypeptide, for instance TNFs or lymphotoxins or anologs of such molecules. The evaluation step, for instance, may further comprise crystallizing the polypeptide in a condition suitable for x-ray crystallography and conducting x-ray crystallography on the polypeptide and its complexes with the candidate substances. Of particular interest will be evaluation of candidate substances capable of determining the ability of the polypeptide to inhibit the undesirable activity of the candidate substance.

A method for assaying a sample for the presence of a cytokine by analyzing the ability of the cytokine to interact with a cytokine receptor polypeptide is also disclosed. This method first requires obtaining a cytokine receptor polypeptide as described herein and then exposing the purified polypeptide to the sample. After the sample is exposed in this manner to the polypeptide, a variety of means may be utilized to evaluate the interaction of the polypeptide with the sample.

A method relating to the use of the chimeric polypeptide of the invention as an anti-tumor reagent is also disclosed. In particular, where a cytokine such as TNF disrupts the physiology of an organ such as the placenta, it is proposed that the cytokine will also disrupt the physiology of trophoblastic tumors such as chorio-carcinomas. Tumors of the placenta, including less malignant varieties such as the chorioadenoma destruens, are likely to be effectively treated by infusion of the TNF inhibitors of the invention. In general, it is likely that clinical benefit may be obtained by inhibiting the biological actions of the TNF that is released from a tumor tissue, including actual inhibition of growth of the tumor.

Additionally, and in a related manner, methods are disclosed for the administration of the TNF inhibitors of the present invention to pregnant mammals in order to interfere with the normal development of pregnancy. In particular, since it is known that the TNF inhibitors of the invention are capable of crossing the placenta and entering the fetal circulation, and since it is known that the portion of the placenta which secretes TNF is the trophoblast (e.g., that part of the placenta which is derived from the conceptus at fertilization), it is likely that infusion of the TNF inhibitors of the invention will disrupt the normal physiology of the growing fetus at or near conception.

BRIEF DESCRIPTION OF THE DRAWINGS

1a. Method used to construct the TNF inhibitor. cDNAs encoding the human TNFR-ED and the murine IgG1 heavy chain hinge and $F_c$ region were separately amplified by PCR using primers which add unique restriction enzyme sites (Cla I on the 5' end of the TNFR-ED and Xba I on the 3' end of the IgG1) and a thrombin sensitive peptide linker (on the 3' end of the TNFR-ED and on the 5' end of the IgG). Following separation of the PCR products by low melting point agarose electrophoresis, slices containing the fragments of interest were combined and subjected to a second round of amplification using only the 5' end primer for TNFR-ED and the 3' end primer for IgG. The PCR products were again separated by agarose electrophoresis and the fragment corresponding to the full length inhibitor was isolated, digested with Cla I and Xba 1, and subcloned into pCMV4. CMV, cytomegalovirus promoter; 5'UTR, 5'untranslated region; T.C.S., thrombin cleavage site; bGH 3'UTR, human growth hormone 3' untranslated region; SV40 ori+enh, simian virus 40 origin of replication and enhancer. The amino acid sequence Leu Val Pro Arg Gly Ser is seq id no:1 and the nucleotide sequence CTG GTT CCG CGT GGA TCC is seq id no:2.

1b. Schematic depiction of the protein. NGF receptor-like cysteine-rich domains of the TNFR-ED are represented by loops. The bars represent the cysteine residues (oxidation state is unknown). IgG moiety is presented according to the same scheme.

Figure 1A:
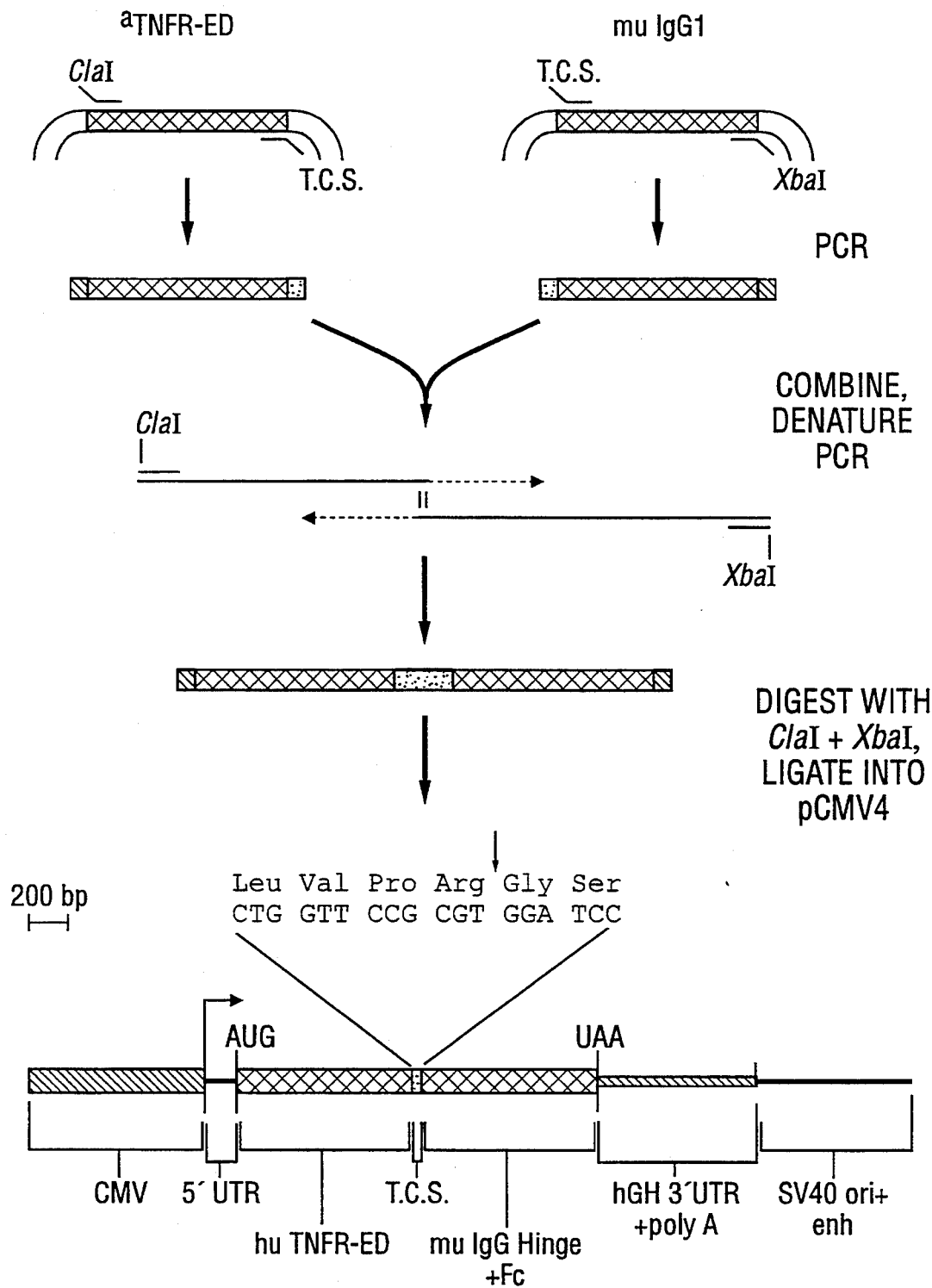

2. Northern blot of TNF inhibitor mRNA produced by transfected CHO cells. 3 μg of total RNA from inhibitor-transfected or control CHO cells of each sample was separated on a 1.2% agarose gel, electroblotted onto nylon, and hybridized either to radiolabeled TNFR-ED antisense RNA (panel A) or to radiolabeled glyceraldehyde-3-phosphate dehydrogenase (GAPDH) antisense RNA (panel B). Arrow indicates the position of the TNF inhibitor mRNA.

3. Inhibition of TNF cytotoxicity by secreted inhibitor. 50 μl of CHO conditioned culture medium (either from cells permanently transfected with the TNF inhibitor cDNA or from control cells transfected with pcDNAneo alone) were incubated with varying amounts of human TNF (concentration indicated) in the presence of cycloheximide. After a one hour incubation at 37° C., $5 \times 10^4$ SK MEL 109 cells were added to the system, and the incubation was continued overnight. Cell survival was quantitated by staining with crystal violet.

4. Purification of the TNF inhibitor by affinity chromatography. Conditioned medium from CHO cells transfected with the TNF inhibitor cDNA was passed over a goat anti-mouse IgG sepharose column. The bound protein was eluted with a solution containing 50 mM acetic acid and 15 OmMNaCl. The eluate was quickly neutralized by adding 1/10 volume of 1M tris, pH 8.0. Inhibitor so purified was subjected to reducing (+β-mercaptoethanol) and nonreducing (-β-mercaptoethanol) SDS-PAGE. 200 ng of a monoclonal anti-TNF antibody (no. 1) was added to the gel as an additional standard. The gel was silver stained.

5. Cleavage of the TNF inhibitor by thrombin. Affinity-purified TNF inhibitor or monoclonal anti-TNF antibody (No. 1) was digested with thrombin for varying lengths of time (indicated) and separated by non-reducing SDS-PAGE. After blotting onto a nitrocellulose membrane, the IgG containing fragments were visualized using an affinity purified goat anti-mouse IgG antibody conjugated to alkaline phosphatase (Biorad). Roman numerals I, II, and III refer, respectively, to the undigested form of the TNF inhibitor, and to forms from which one or both TNFR-ED have been removed by the action of thrombin. IgG remains undigested in the presence of thrombin.

6. Crosslinking of TNF and inhibitor. Lane a, $^{125}$I TNF not crosslinked; lane b, 1211 TNF crosslinked with DSS; lane c, $^{125}$I TNF crosslinked to inhibitor; lane d, same as lane c but unlabeled TNF was included as competitor; lane e, $^{125}$I TNF crosslinked to thrombin digested inhibitor; lane f, same as lane e but unlabeled TNF was included as competitor.

7. Inhibition of TNF cytotoxicity by inhibitor or extracellular domain. 600 pM inhibitor or 600 pM of inhibitor cleaved with thrombin were incubated with different amounts of TNF (indicated) in the presence of CHX for 1 h at 37° C. $5 \times 10^4$ SK MEL 109 cells were added to each well and incubated overnight. Thrombin alone does not effect survival of SK MEL 109 cells in this assay (data not shown). Cell survival was quantitated by staining with crystal violet.

8. Comparison of anti-TNF activity of two monoclonal antibodies against TNF with the activity of the TNF inhibitor. Varying amounts of antibody or TNF inhibitor were incubated with human TNF (300 pg/ml) in the presence of cycloheximide for one hour at 37° C. $5 \times 10^4$ SK MEL 109 cells were then added to the system, and the incubation was continued overnight. Cytotoxicity was quantitated by staining with crystal violet.

DESCRIPTION OF PREFERRED EMBODIMENTS

As will be described in detail below, the compositions of matter and methods of the present invention are generally applicable to cytokine receptors regardless of the source or the precise sequence of the receptor molecule. Therefore, there are a number of generally applicable techniques which may be used and which are described below. Additionally, examples are provided illustrating the applicability of the general techniques to several specific cytokine receptor polypeptides.

Host Cell Cultures and Vectors

In general, of course, prokaryotes are preferred for the initial cloning of DNA sequences and constructing the vectors useful in the invention. For example, *E. coli* K12 strains may be particularly useful. Other microbial strains which may be used include *E. coli* B, and *E. coli* X1776 (ATCC No. 31537). These examples are, of course, intended to be illustrative rather than limiting.

Prokaryotes may also be used for expression. The aforementioned strains, as well as *E. coli* W3110 (F-, lambda-, prototrophic, ATCC No. 273325), bacilli such as *Bacillus subtilus*, or other enterobacteriacea such as *Salmonella typhimurium* or *Serratus marcesans*, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells.

For example, *E. coli* is typically transformed using pBR322, a plasmid derived from an *E. coli* species (Bolivar et al., 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the β-lactamase (penicillinase) and lactose promoter systems (Chang et al., 1978; Itakura et al., 1977; Goeddel et al., 1979; Goeddel et al., 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to ligate them functionally with plasmid vectors (Siebwenlist et al., 1980).

In addition to prokaryotes, eukaryotic microbes, such as yeast cultures may also be used. *Saccharomyces cerevisiase* or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trp1 gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequences desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers et al., 1978). Smaller or larger SV40 fragments may also be used, provided there is included the approximately 250 bp sequence extending from the HindIII site toward the BglI site located in the viral origin or replication. Further, it is also possible, and often desirable, to utilize promoter or control sequences normally associated with the desired gene sequence, provided such control sequences are compatible with the host cell systems.

An origin of replication may be provided with by construction of the vector to include an exogenous origin, such as may be derived from SV40 or other viral (e.g., Polyoma, Adeno, VSV, BPV, CMV, baculovirus) source, or may be provided by the host cell chromosomal replication mechanism. If the vector is integrated into the host cell chromosome, the latter is often sufficient.

pCMV Eukaryotic Expression Vectors

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region above each plasmid. The pCMV4 vector differs from these 4 plasmids in containing a translation enhancer in the sequence prior to the polylinker. While they are not directly derived from the pCMV1-5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin or replication for production of single stranded DNA and an ampicillin-resistance gene. The CMV region consists of nucleotides −760 to +3 of the powerful promote-regulatory region of the human cytomegalovirus (Towne stain) major immediate early gene (Thomsen et al., 1984; Boshart et al., 1985). The polylinker region may be synthesized on an Applied Biosystem's machine. The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguished from each other by which restriction enzyme sites are unique in the polylinker and by the presence or absence of the translation enhancer. The starting pCMV1 plasmid has been progressively modified to render unique an increasing number of sites in the polylinker. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5'-untranslated region of a mRNA transcribed from the CMV promoter. The sequence acts as a translational enhancer by decreasing the requirements for initiation factors in protein synthesis (Jobling et al., 1987); Browning et al., 1988). To create pCMV5, a segment of DNA (HpaI to EcoRI) was deleted from the SV40 origin region of pCMV1 to render unique all sites in the starting polylinker.

The pCMV vectors have been employed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, G$_S$, alpha protein, protein phosphatase, synaptophysin, synapsin, insulin receptor, flu hemmagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites that may cause spurious translation initiation. This codon should be avoided if possible in expression plasmids. A paper describing the construction and use of the parenteral pCMV1 and pCMV4 vectors has been published (Andersson et al., 1989b).

Biological Functional Equivalent Amino Acids

As noted above, it is believed that, where desired, modification and changes may be made in the structure of the cytokine receptor polypeptide and still obtain a molecule having like or otherwise desirable characteristics. Such changes may occur in natural isolates or may be synthetically introduced using site-specific mutagenesis as described below.

For example, certain amino acids may be substituted for other amino acids in a protein structure without appreciable loss of interactive binding capacity with structures such as antigen-binding regions of antibodies (or, e.g., binding sites on substrate molecules). Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the peptides (or underlying DNA) without appreciable loss of their biological utility or activity.

The importance of the hydropathic index of amino acids in conferring interactive biologic function on a protein has been discussed generally by Kyte et al. (1982), or U.S. Pat. No. 4,554,101 to Hopp, both incorporated herein, wherein it is found that certain amino acids may be substituted for other amino acids having a similar hydropathic index or score and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

TABLE I

| AMINO ACID | HYDROPATHIC INDEX |
| --- | --- |
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

It is proposed that where an amino acid has a hydropathic index of within ±2 that of the base amino acid, and more preferably within ±1, such a change should nevertheless provide a protein having a similar, and perhaps even improved, functional activity. Thus, for example, it is proposed the isoleucine, which has a hydropathic index of +4.5, can be substituted for valine (+4.2) or leucine (+3.8), and still obtain a protein having similar biologic activity. Alternatively, at the other end of the scale, it is proposed that lysine (−3.9) can be substituted for arginine (−4.5), and so on.

Accordingly, these amino acid substitutions are generally based on the relative similarity of R-group substituents, for example, in terms of size, electrophilic character, charge, and the like. In general, exemplary substitutions which take various of the foregoing characteristics into consideration include the following:

TABLE II

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |

TABLE II-continued

| Original Residue | Exemplary Substitutions |
|---|---|
| Tyr | Trp; Phe |
| Val | Ile; Leu |

Site-Specific Mutagenesis

Site-specific mutagenesis is a technique useful in the preparation of second generation proteins, or biologically functional equivalent proteins or peptides, derived from the sequences thereof, through specific mutagenesis of the underlying DNA. As noted above, such changes may be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman et al., (1983). As will be appreciated, the technique typically employs a phage vector which exist in both a single stranded and double stranded form. Typical vectors useful in site-directed mutagenesis include vectors such as the M13 phage (Messing et al., 1981). These phage are readily commercially available and their use is generally known to those of skill in the art.

In general, site-directed mutagenesis in accordance herewith is performed by first obtaining a single-stranded vector which includes within its sequence a DNA sequence which encodes all or a portion of the cytokine receptor polypeptide sequence selected. An oligonucleotide primer bearing the desired mutated sequence is prepared, generally synthetically, for example, by the method of Crea et al., (1978). This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutated sequence arrangement.

Screening Assays

An important aspect of the invention is the use of recombinantly produced cytokine receptor polypeptides in screening assays for the determination of the presence of TNF-like molecules and in the identification of substances which may inhibit or otherwise modify or alter the function of the receptor. The use of recombinantly produced receptor is of particular benefit because the naturally occurring receptor is present in only small quantities and has proven difficult to purify. Moreover, this allows one a ready source of human receptor, which have heretofore been lacking.

The screening assays of the invention, in preferred embodiments, will conveniently employ the receptor polypeptide directly from the recombinant host in which it is produced. This is achieved most preferably by simply expressing the selected polypeptide within the recombinant host, typically a eukaryotic host, followed by preparing a sample of the cell culture medium which includes the secreted chimeric polypeptide. A portion of the culture medium may then be admixed with an appropriate effector of the receptor, e.g., cytokine, TNF, lymphotoxins, etc. Alternatively, an additional purification step is accomplished on the culture medium containing the chimeric polypeptide in order to recover a purified quantity of chimeric polypeptide molecules. The additional purification steps may include specific binding of the chimeric molecules to protein A, anti-mouse IgG or, using affinity chromatography with a lectin column such as concanavalin A or lentil lectin. By comparing the binding of the selected effector (for instance, TNF or lymphotoxin) in the presence or absence of the candidate substance (for instance, a TNF agonist or antagonist) one can obtain information regarding the binding properties of the candidate substance.

There are believed to be a wide variety of embodiments which can be employed to determine the effect of the candidate substance on the receptor polypeptides of the invention, and the invention is not intended to be limited to any one such method. However, it will generally be desirable to employ a system wherein one can measure the ability of the receptor polypeptide to bind to and or be modified by the effector employed to a particular substance. One method which may be employed may use a labeled effector, which has been labeled in a manner such that the label is quantitatively retained in the resultant effector/receptor complex. A convenient approach is the use of a radioactive label, such as $^{125}I$, $^{14}C$ or $^{3}H$, which may be directly quantitated in both the effector and the resultant complex.

In preferred assays, the admixture containing the protein, effector and candidate substance is allowed to incubate for a selected amount of time, and the resultant incubated mixture subjected to a separation means in order to separate the unbound effector remaining in the admixture from any effector/receptor complex so produced. Then, one simply measures the amount of each, e.g., versus a control to which no candidate substance has been added. This measurement can be made at various time points where velocity data is desired. From this, one may determine the ability of the candidate substance to alter or modify the function of the receptor.

Numerous techniques are known which could be employed for the separation of the effector from effector/receptor complex, and all such methods are intended to fall within the scope of the invention. Use of thin layer chromatographic methods (TLC), HPLC, spectrophotometric, gas chromatographic/mass spectrophotometric or NMR analyses. Other, more specific methods of purification already noted (affinity binding or immunoprecipitation) may be used, as well. It is contemplated that any such technique may be employed so long as it is capable of differentiating between the effector and complex, and can be used to determine enzymatic function such as by identifying or quantifying the substrate and product.

The effector/receptor complex itself may also be the subject of techniques such as x-ray crystallography. Where a candidate substance replaces the effector molecule as the drug's mode of action, studies designed to monitor the replacement and its effect on the receptor will be of particular benefit.

EXAMPLES

Examples have been included in order to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

I. CONSTRUCTION OF A CHIMERIC CYTOKINE RECEPTOR REAGENT

Cell culture

The human skin melanoma cell line SK MEL 109 was grown in FM medium supplemented with 10% fetal bovine serum (FBS). CHO cells were grown in F12 medium supplemented with 10% FBS. Transfected CHO cells were grown in monolayer or spinner cultures. For production of the TNF inhibitor, CHO cells in spinner culture were maintained in serum free medium (90% F12 and 10% complete WRC 935 medium) for three days, after which cells were removed and the conditioned medium, containing the inhibitor, was processed.

Cloning of a CDNA encoding the TNF receptor extracellular domain (TNFR-ED)

The TNFR-ED was cloned from total cytoplasmic RNA prepared from HL60 cells using a reverse transcriptase/polymerase chain reaction protocol (Kawasaki 1990). Briefly, an oligonucleotide primer with the following sequence (seq. id no:3):

cttaagcttagtactcaTGTGGTGCCTGAGTCCT-CAG corresponding to the 3' end of the extracellular domain was used to direct first strand CDNA synthesis in a total volume of 20 IAI. The reaction was then diluted to 100 ug in PCR buffer and a second primer with the following sequence (seq. id no.: 4):

gcgcatcgaTCTGGCATGGGCCTCTCCACC corresponding to the 5' end of the human TNF receptor was added. The reaction was subjected to 40 cycles of denaturation and synthesis in an automated temperature cycler (Perkin Elmer Cetus Corp.). The band corresponding to the TNFR-ED was purified by gel electrophoresis and ligated into the vector pGEM-3Z.

Preparation of the chimric construct

A plasmid encoding a murine IgG1 heavy chain cDNA was obtained using techniques known well to those of skill in the art. The TNFR-ED and the IgG heavy chain cDNAs were separately amplified by PCR using primers:

gcgcatcgaTCTGGCATGGGCCTCTCCACC (seq. id no:4, corresponding to the 5' end of the TNFR-ED moiety), ggatccacgcggaaccagTGTGGTGCCT-GAGTCCTC seq. id no. 5, (corresponding to the 3' TNFR-ED moiety and the thrombin cleavage site), ctggttccgcgtggatccGTGCCCAGGGATTGTGGT (seq. id no.: 6, corresponding to the thrombin cleavage site and the 5' end of the IgG moiety), and attaagcattctagatcatttaccaggagagtg (seq. id. no.: 7, corresponding to the 3' end of the IgG moiety).

Figure 1B:
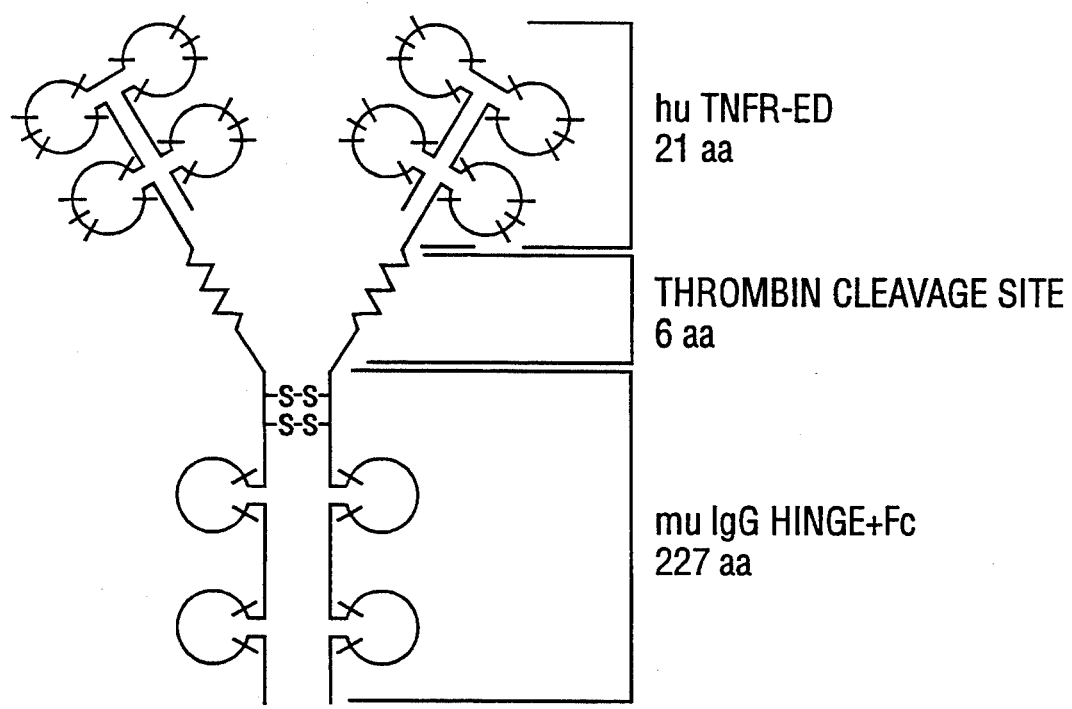
Figures 2A, 2B:
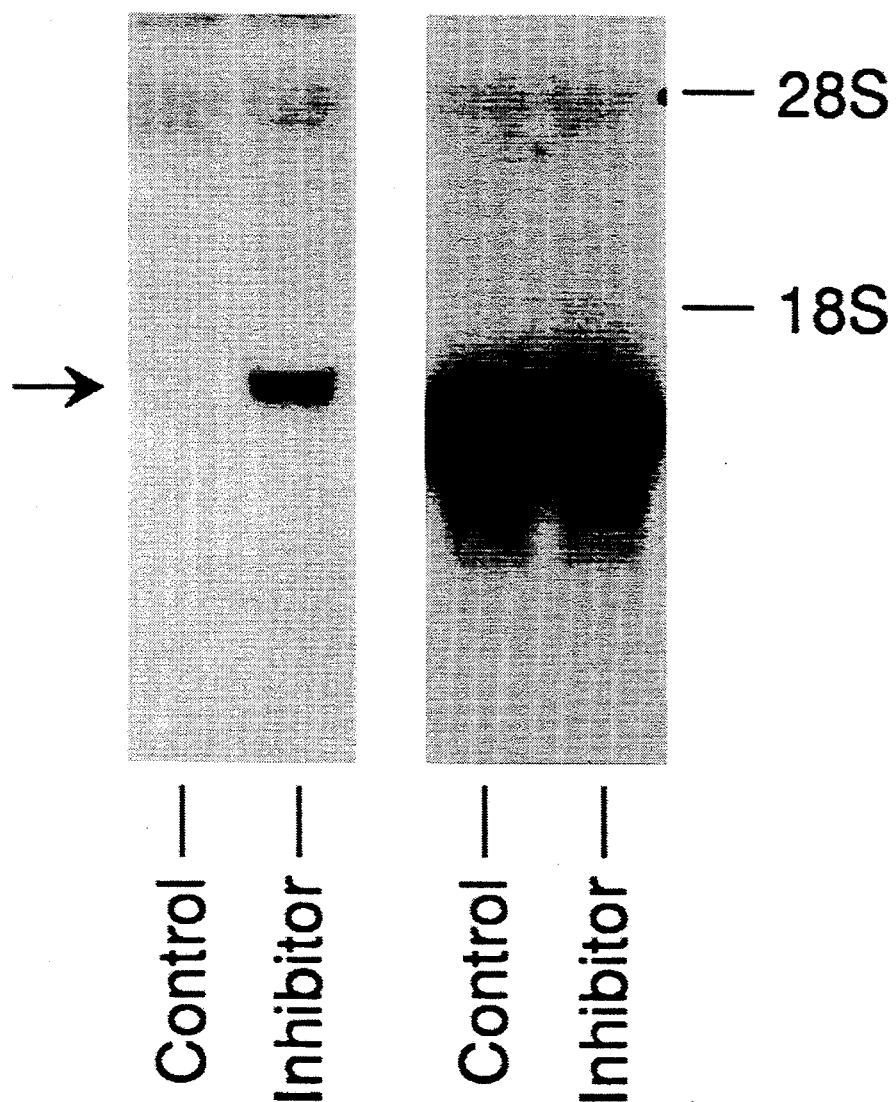
Figure 3:
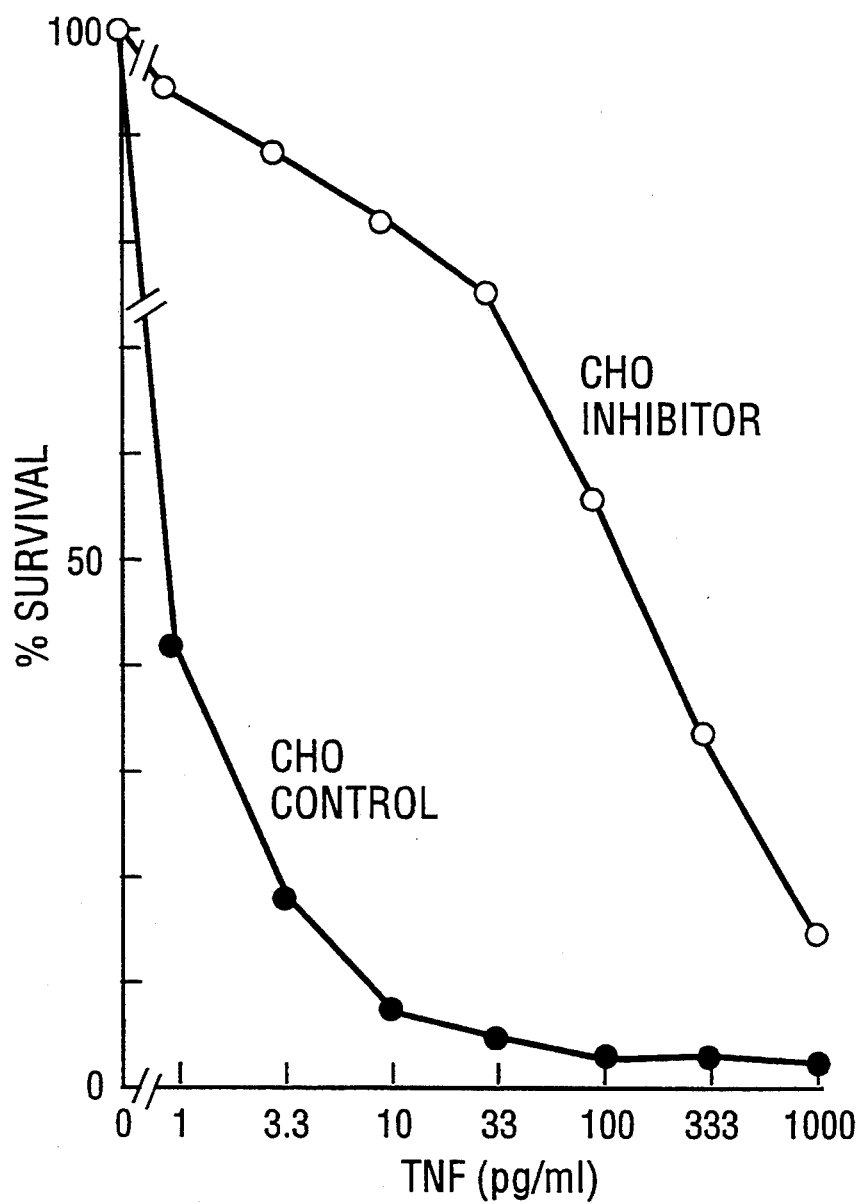
Figure 4:
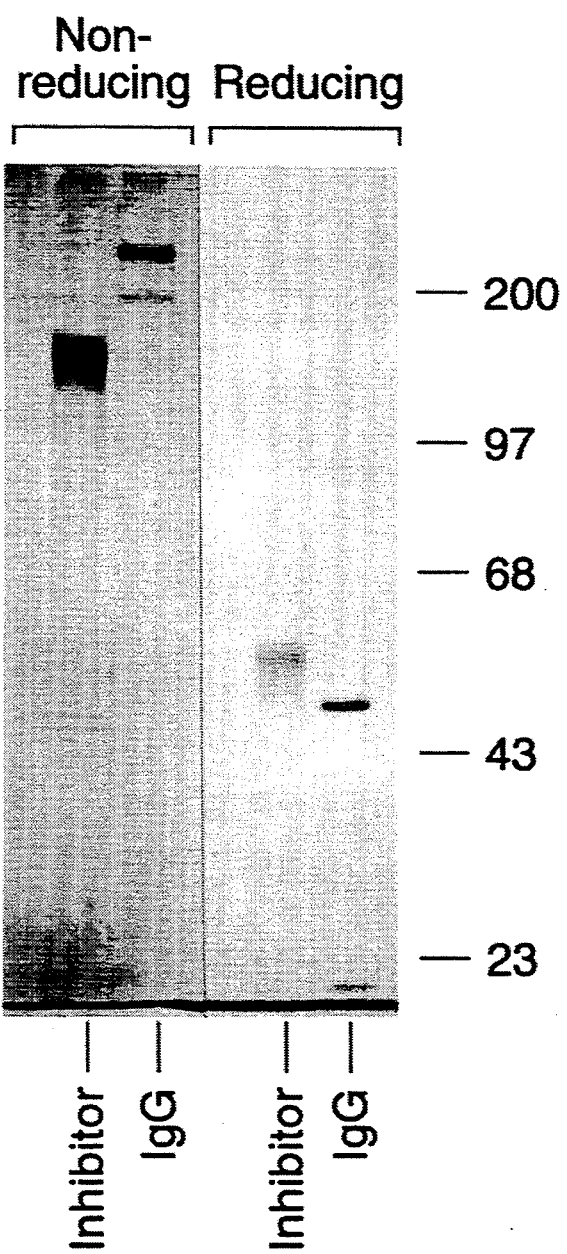
Figure 5:
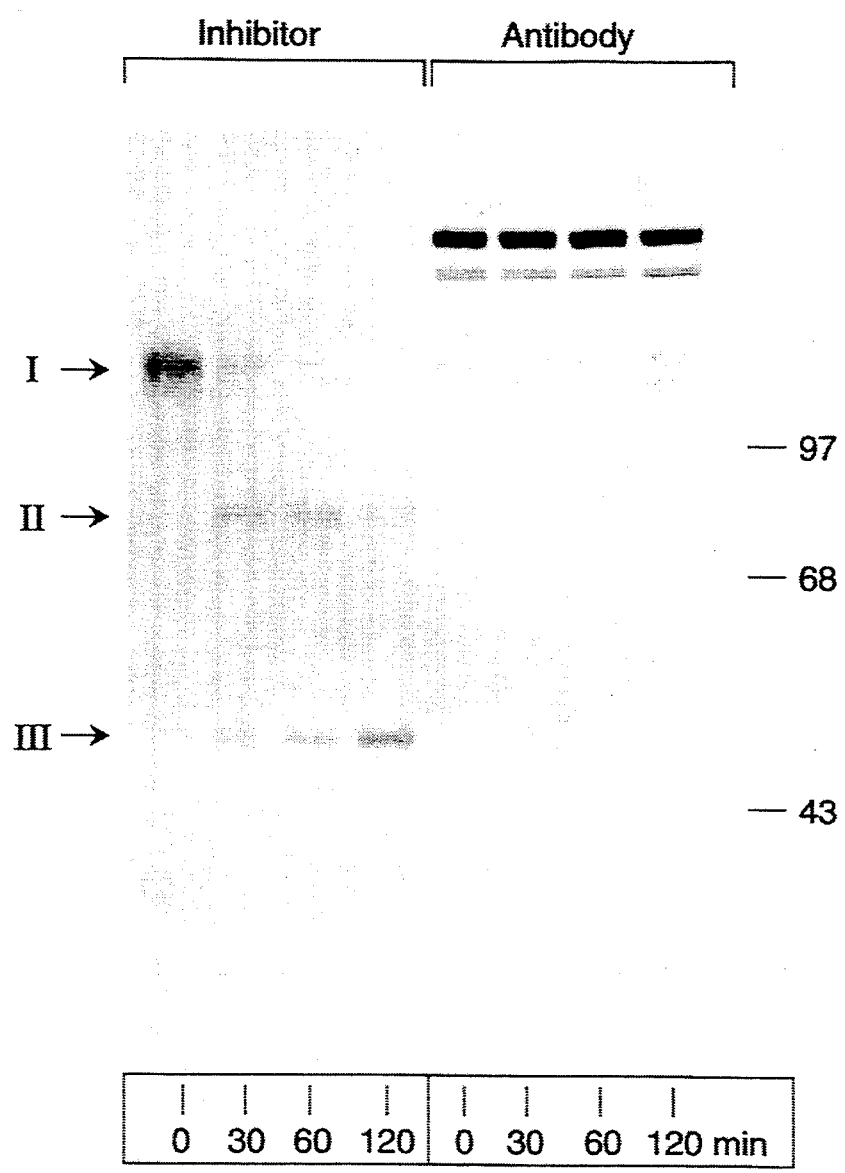
Figure 6:
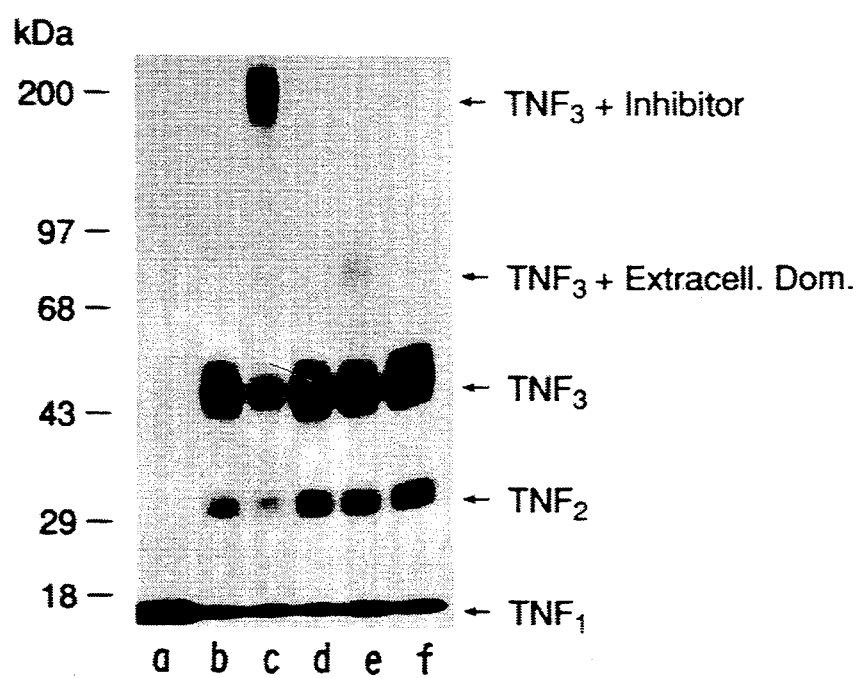
Figure 7:
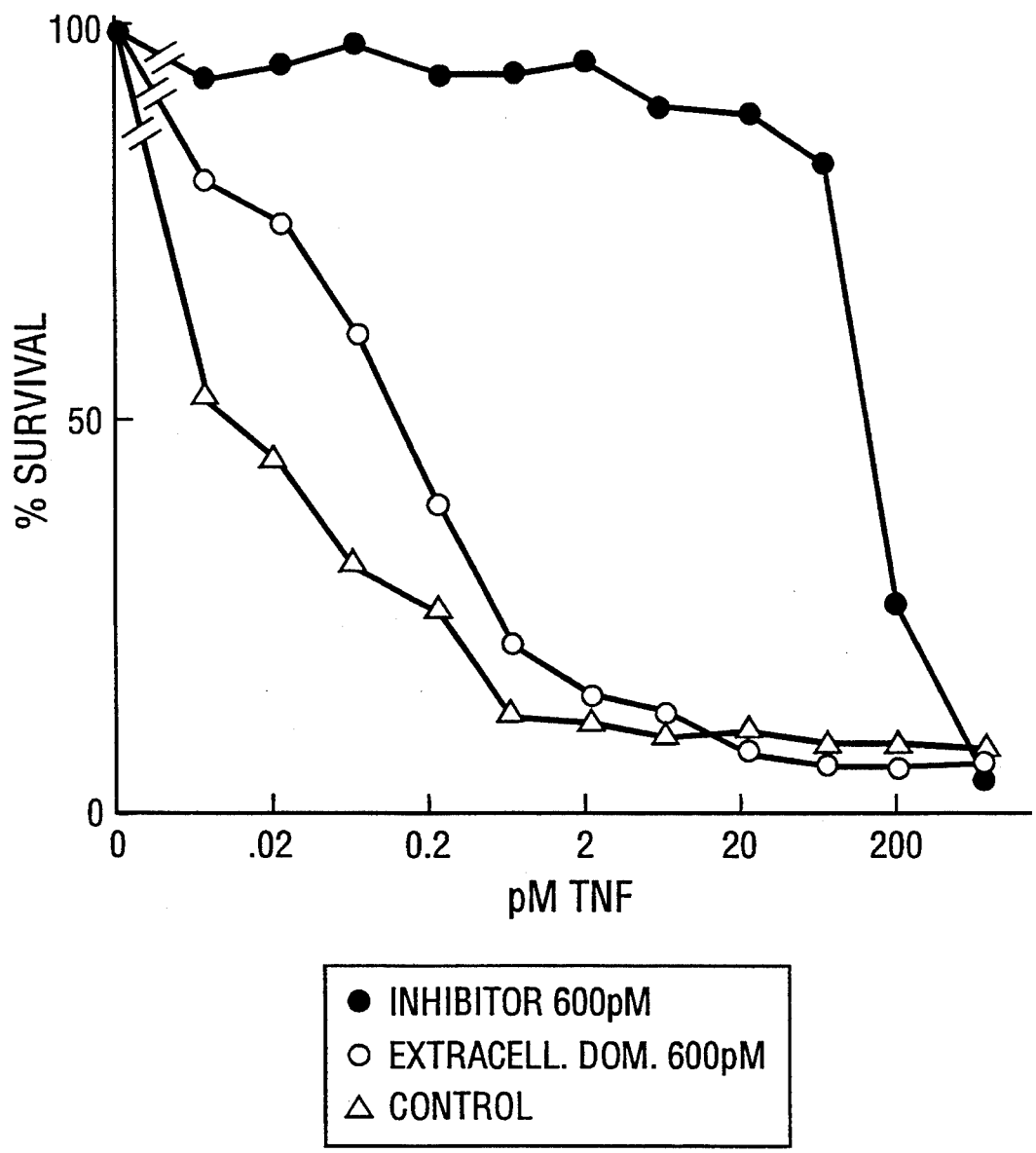
Figure 8:
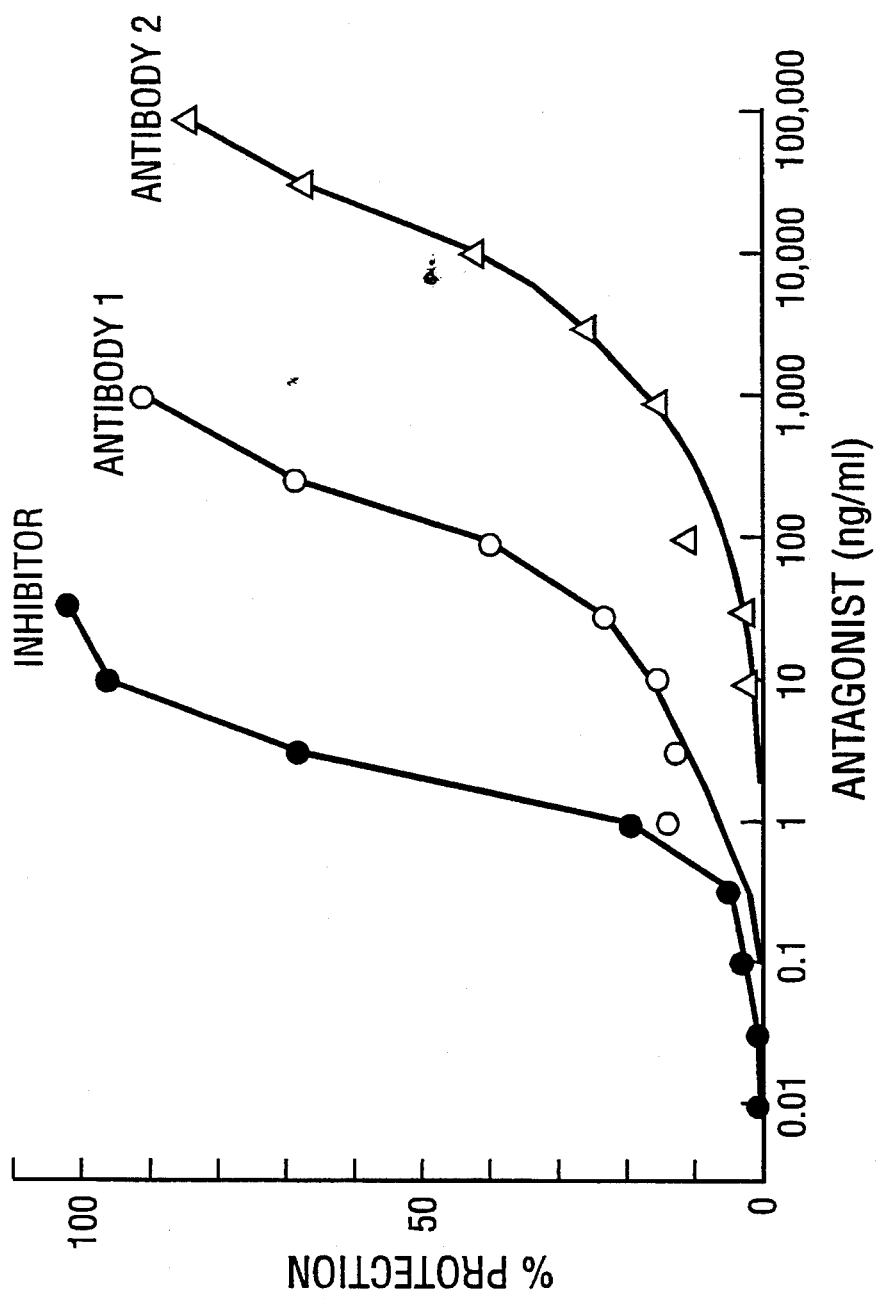

As schematically illustrated in FIG. 1, the PCR products obtained after the first synthetic PCR reaction thus carry the thrombin cleavage site on their 3' (TNFR-ED) and 5' (IgG) ends. The PCR products were isolated on a low melting point gel and slices containing the correct DNAs were combined and used for a second round of PCR amplification, using only primers corresponding to the 5' end of the TNFR-ED and 3' end of the IgG.

This PCR reaction effectively joins the TNFR-ED and the IgG through the thrombin cleavage site.

The construct was then digested with Cla I and Xba I (encoded in the 5' TNFR-ED and 3' IgG primers) and ligated into the vector pCMV4 (Andersson et al. 1989). The entire sequence was verified by dideoxynucleotide sequencing (Sanger et al. 1977) on both strands.

Assays of TNF and TNF inhibitor activity

TNF inhibitor activity was determined through inhibition of TNF cytotoxicity toward human SK MEL 109 cells in the presence of the protein synthesis inhibitor cycloheximide (CHX). Typically, a constant amount of inhibitor was incubated with a series of standard concentrations of TNF in FM medium containing 10% FBS and CHX at a final concentration of 50 $\mu$g/ml. The final system volume was 150 $\mu$l. TNF was allowed to preincubate with the inhibitor for 12 hours or for 1 hour (FIG. 3,6,7,8) at 4° C. in a 96 well microtiter plate. 50 $\mu$l of FM containing 10% FBS and $5 \times 10^4$ SK MEL 109 cells was then added to each well. A further incubation was then carried out overnight at 37° C. in a 5% $CO_2$ incubator. At the end of the incubation the plate was washed and stained with crystal violet. The cell-bound dye was dissolved in 40% acetic acid and staining was quantitated in an automatic plate reader. All assays were performed in duplicate and the standard error in all experiments was less than 10%. Monoclonal antibodies against TNF were used for comparative purposes in some assays. One such antibody (designated monoclonal no. 1) may be obtained from Suntori, Inc (Japan). A second antibody (SW 18.1; here designated monoclonal no. 2) may be obtained from Genetics Institute (Cambridge, Mass.). A third antibody (designated monoclonal no. 3) may be obtained from R. Schreiber (Washington University, St. Louis, Miss.) which neutralize mouse TNF. However, it will be understood by those of skill in the art that any of a number of anti-TNF antibodies may be used. Such antibodies may be generated by standard protocols known well to those of skill in the art by obtaining a purified source of TNF as noted herein and using this as an antigen in the production of a monoclonal antibody (see, e.g. *Monoclonal Antibodies—Hybridomas: A new Dimension in Biological Analyses*, R. H. Kennettt, T. J. McKearn and K. B. Bechtol, Eds., Plenum Press, N.Y., 1981). Monoclonals 1 and 2 neutralize human TNF, whereas monoclonal 3 neutralizes mouse TNF.

CHO cell transfection

CHO cells were cotransfected with the inhibitor cDNA in pCMV4 (pCMV4-1), and with the vector pcDNAneo, in a 10:1 ratio, or with pcDNAneo alone, using the calcium phosphate precipitation method of Chen and Okayama (1987). Cells resistant to 1 mg/ml G418 were selected over a 3 week period and pooled. Each transfection yielded approximately 200–300 independent transfectants.

Northern blot analysis

Total cytoplasmic RNA was prepared from transfected CHO cells as previously described (Peppel 1991). For Northern analysis the RNA was glyoxylated, resolved in a 1.2% agarose gel, and electroblotted onto a nylon membrane. It was then hybridized to $^{32}$P-labeled antisense riboprobes corresponding to the TNFR-ED or to human glyceraldehyde-3phosphate dehydrogenase (GAPDH). After hybridization the blot was washed twice in 2×SSC at 70° C. and finally in 0.1×SSC at 70° C. Blots were allowed to expose x-ray film overnight at −80° C.

Production and purification of the chimetic TNF inhibitor

For production of inhibitor cells were incubated in serum free medium (90% F12:10% complete WRC 935) for 72 hours. Cells were then removed by centrifugation followed by filtration. The conditioned medium was then passed over a column of goat anti-mouse heavy chain IgG coupled to sepharose (Sigma Chemical Co.). The affinity resin was then washed with a solution containing 500 mM NaCl, 10 mM NaH$_2$pO$_4$ (pH 7.2), and 1 mM EDTA. Bound protein was eluted with a solution containing 50 mM acetic acid (pH 2.4) and 150 mM NaCl. 500 μl fractions were collected and neutralized by addition of 75 μl of 1 M Tris (pH 8.0). Fractions were dot-blotted onto nitrocellulose and incubated with alkaline phosphatase conjugated goat anti-mouse IgG to permit detection and quantitation of the inhibitor.

Thrombin cleavage

100 μl of column eluate containing approximately 300 ng pure inhibitor was mixed with 100 μl of digestion buffer (at 10 mM CaCl$_2$, 10 mM MgCl$_2$, and 100 mM tris, pH 7.0). 5 μl of a preparation containing 0.5 units of thrombin (Boehringer) was then added and the reaction was incubated at 25° C. for various periods of time. Aliquots were removed at intervals and the reaction was terminated by the addition of SDS sample buffer.

Iodination of TNF

Human recombinant TNF was iodinated using the iodogen method (Fraker and Speck 1978). Radiolabeled TNF was separated from unincorporated $^{125}$I by chromatography on Sephadex G25. The specific activity of the final preparation was $1\times10^4$ cpm/ng TNF.

Crosslinking of TNF to Inhibitor 25 ng of $^{125}$I TNF was incubated for 1 h at 37° C. with 100 ng of purified inhibitor, or inhibitor that had been cleaved with thrombin, in 50 μl of buffer (25 mM Hepes, pH 7.2, 5 OmM NaCl, 0.1% BSA). Where indicated 2 μg of unlabeled competitor TNF was included in the reaction. 2.5 μl of disuccinimidylsuberate (DSS; (Pierce Chemical Co.) 9.3 mg/ml in DMSO) was added and the reaction was incubated for 30 minutes at 37° C. The reaction was then terminated by the addition of SDS sample buffer.

SDS-polyacrylamide gel electrophoresis (PAGE)

SDS-PAGE of the inhibitor and of mouse IgG, before and after thrombin cleavage, under reducing and non-reducing conditions, was carried out as previously described (Laemmli 1970). Western blot analysis was performed after electrotransfer of the protein to nitrocellulose membranes. An alkaline phosphatase-conjugated goat anti-mouse IgG was used to detect the chimeric receptor-IgG proteins.

In vitro translation

A 2.7 kb Sac I fragment containing the entire inhibitor cDNA was subcloned into pGEM4. After linearization with Xho 1, the plasmid was transcribed in vitro with SP6 polymerase in the presence of m7GpppG to yield 5'-capped RNA transcripts. 1/5 of the transcription reaction was used to program rabbit reticulocyte lysates (Promega Biologicals) in a standard translation reaction prepared according to instructions provided by the manufacturer in the presence of $^{35}$S translabel (obtained from ICN Chemicals). After synthesis, the proteins were resolved by SDS-PAGE and analyzed by autoradiography.

Cloning of the TNF Chimeras into Baculovirus Vectors

The DNA for the TNF-Inhibitor was amplified by PCR using primers that added a BclI site (5' end, compatible with BglII site in the polylinker of pVL 1392) and an XbaI site (3' end, present in polylinker of pVL 1392). This amplified DNA was digested with BclI and XbaI and subcloned into BglII and XbaI digested pVL 1392. This plasmid was mixed with baculovirus DNA (Bsu36I digested AcRP23-LacZ viral DNA) and used to transfect Sf9 insect cells by the lipofectin method. Recombinant vital plaques were identified by their lack of B-galactosidase activity (the non-recombinant viral plaques will stain blue if X-gal is provided as substrate, whereas the recombinant viral plaques will stain clear or white). Sf9 or Sf21 cells secrete the TNF inhibitor into the culture medium after infection with the recombinant baculovirus. The protein is purified from the medium by adsorption and elution from a protein A-Sepharose column followed in some cases by adsorption and elution from a goat anti-mouse IgG antibody column (general reference to protein expression using the baculovirus expression system—Summers and Smith (Tex. Agric. Exp. Stn. Bull. 55:1–56(1987); protocols and descriptions of viral vector AcRP23-LacZ - Nucl. Acids Res. 15:10233 (1987); Nucl. Acids Res. 18:4033 (1990); Nucl. Acids Res. 18:5667 (1990)).

II. USE OF THE CYTOKINE RECEPTOR CHIMERIC REAGENT AS A BIRTH CONTROL REAGENT

In many ways, the implantation and growth of an embryo resembles the growth of a tumor in the wall of the uterus. Since the reagents of the invention have been successfully used to limit tumor growth of placental tumors, it is predicted that the reagent may find usefulness in preventing pregnancy.

It has been noted that the human placenta constitutively secretes tumor necrosis factor, and evidence related to its production of other cytokines including IL-4 and GM-CSF has also been presented. Studies carried out by the present inventors suggest that the portion of the human placenta that secretes TNF is that part known as the trophoblast (e.g., that part of the placenta that is derived from the conceptus at fertilization). The maternal portion of the placenta (the decidua) does not produce TNF constitutively.

TNF might fulfill an essential function within the placenta. This function might relate to maintenance of the immune barrier between the mother and the histoincompatible fetus, or might relate to growth and development of the placenta.

In any case, the function of TNF was investigated in the placenta by administering antibody against TNF, and also the TNF receptor chimeric polypeptide to pregnant mice. This reagent served to terminate pregnancy in 4 out of 4 mice studied. In some instances, fetuses were observed in varying stages of resorption. In other instances, no fetal tissue was observed, and the uterus was enlarged and fluid filled.

In separate studies, it was demonstrated that the chimeric TNF receptor is capable of crossing the placenta and entering the fetal circulation. This was assessed by injecting a pregnant mother with the inhibitor, and, after a period of time, bleeding this animal (sacrificing her) and assaying inhibitor levels both in her circulation and in the blood of the fetuses. These data lead the present inventors to believe that TNF fulfills an essential function during pregnancy and that disruption of this function by administration of the chimeric inhibitor will lead to termination of pregnancy. These results should be applicable to other species as well.

III. CLINICAL USE OF THE CHIMERIC RECEPTOR POLYPEPTIDE AS AN ANTI-TUMOR AGENT FOR PLACENTAL TUMORS

If TNF inhibitor disrupts the physiology of the placenta, it is likely that it will also disrupt the physiology of trophoblastic tumors (e.g., choriocarcinomas). These tumors, and less malignant tumors of the placenta such as the chorioadenoma destruens, might be effectively treated by infusion of TNF inhibitor. It has been shown that certain trophoblastic tumors of mice do, indeed, secrete TNF. Other tumors also secrete TNF. These include the L-929 cell line (a mouse fibrosarcoma) and a certain breast tumor as well. Certain hematologic malignancies may also secrete TNF. In all cases, clinical benefit might be obtained by inhibiting the biological actions of the TNF that is released, and in some instances, the clinical benefit might include inhibition of the growth of the tumor.

IV. Assays of TNF in Serum

Assays of TNF in serum samples will be conducted by producing an endogenously labelled chimeric TNF receptor polypeptide. Endogenous labelling may be accomplished by incorporation of $^{35}$S or other radioisotopes, or by incorporation of colorimetric labelling. Where $^{35}$S is used for endogenous labelling, the radioisotope is provided to the host cell and is thereby incorporated during protein synthesis into the cysteine and methionine residues within the polypeptide.

The ligand, which is preferably labelled to a very high specific activity, is mixed with the serum sample to be assayed. After incubating the labelled polypeptide together with the serum, a specific anti-mouse IgG antibody capable of specifically binding the IgG portion of the chimeric polypeptide, is added to the sample. The anti-IgG antibody is preferably bound to a solid phase matrix such as Agarose or SEPHAROSE™ beads. Immunoprecipitation is allowed to occur. A cross-linking agent, such as disuccinyl suberate (DDS) is next applied to the immunoprecipitate so as to fix the soluble receptor to any adherent chimeric polypeptide. The immunoprecipitate is then dissolved in a buffer containing sodium dodecyl sulfate (or other suitable solubilizing agent) and subjected to gel electrophoresis such as polyacrylamide gel electrophoresis, under protein denaturing conditions. Positive identification of the active form of the cytokine in the serum sample would be visible as a shift in the mobility of the radio labelled ligand to a higher molecular weight position on the gel. This shift would result from the binding of soluble, active cytokine to the soluble cytokine receptor.

REFERENCES CITED

The following references to the extent that they provide procedural details supplementary to those set forth herein, are specifically incorporated herein by reference.

Andersson et al., *J. Biol. Chem.* 264:8222 (1989)
Beutler et al., *J. Exp. Med.*, 161:984 (1985)
Beutler et al., *Nature*, 320:584–588 (1986)
Beutler et al., *Ann. Rev. Biochem.*, 57:505–518 (1988)
Capon et al., *Nature*, 337:525 (1989)
Chen et al., *Mol. Cell. Biol.*, 7:2745 (1987)
Dembic et al., *Cytokine*, 2:231 (1990)
Eades et al., *Placenta*, 9:247–251 (1988)
Engelmann et al., *J. Biol. Chem.*, 264:11974 (1989)
Engelmann et al., *J. Biol. Chem.*, 265:14497 (1990)
Fraker et al., *Biochem. Biophys. Res. Commun.*, 80:849 (1978)
Jäättelä et al., *Lab. Invest.* 58:48–52 (1988)
Kawasaki, E. S., (1990) Amplification of RNA. In PCR Protocols, M. A. Innis, D. H. Gelfand, J. J. Sninsky, and T. J. White, editors. Academic Press, Inc., San Diego. 21.
Kobno et al., *Proc. Natl. Acad. Sci.*, 87:8331 (1990)
Laemmli, U.K. *Nature*, 227:680 (1970)
Liabakk et al. *J. Immunol. Methods*, 134:253–259 (1990)
Loetscher et al., *Cell*, 61:351 (1990)
Loetscher et al., *J. Biol. Chem.*, 265:20131 (1990)
Oliff et al., *Cell*, 50:555 (1987)
Ostade et al., *EMBO*, 10:827 (1991)
Peppel et al., *J. Exp. Med.*, 173:349 (1991)
Sackinger et al., *J. Biol. Chem.*, 264:11966 (1989)
Sanger et al., *Proc. Natl. Acad. Sci.*, 74:5463 (1977)
Schall et al., *Cell*, 61:361 1990

Shirai et al., *Nature*, 313:803–806 (1985)
Smith et al., *J. Biol. Chem.* 261:14871 (1986)
Smith et al., *J. Biol. Chem.*, 264:14646 (1989)
Smith et al., *Science*, 248:1019 (1990)
Traunecker et al., *Nature*, 339:68 (1989)

The present invention has been described in terms of particular embodiments found or proposed to comprise preferred modes for the practice of the invention. It will be appreciated by those of skill in the art that, in light of the present disclosure, numerous modifications and changes can be made in the particular embodiments exemplified without departing from the intended scope of the invention. For example, other disease states including cachexia, endotoxin shock, and hypercalcemia of malignancy all of which have been implicated in TNF reactions, may be effectively treated by the use of the reagents and methods of the present invention. All such modifications are intended to be included within the scope of the appended claims.

---

What is claimed is:

1. An isolated DNA segment having a sequence encoding a chimeric polypeptide comprising the extracellular domain of a TNF receptor polypeptide functionally attached to a Fc portion and hinge region of an IgG heavy chain polypeptide.

2. The isolated DNA segment of claim 1, where the TNF receptor polypeptide is a human TNF receptor polypeptide.

3. The isolated DNA segment of claim 1, where the IgG heavy chain polypeptide is a mouse IgG polypeptide.

4. The isolated DNA segment of claim 1, further incorporating a DNA segment encoding a specifically cleavable linker peptide functionally interposed between the TNF receptor polypeptide and the Fc portion.

5. The isolated DNA segment of claim 4, where the specifically cleavable linker peptide comprises a thrombin-sensitive linker peptide.

6. A recombinant vector incorporating a DNA segment as defined by claim 1.

7. The recombinant vector of claim 6, where the TNF receptor polypeptide is a human TNF receptor polypeptide.

8. The vector of claim 6, where the IgG heavy chain polypeptide is a mouse IgG polypeptide.

9. The vector of claim 6, further incorporating a specifically cleavable linker peptide functionally interposed between the extracellular domain of the TNF receptor polypeptide and the Fc portion.

10. The vector of claim 9, where the specifically cleavable linker peptide comprises a thrombin-sensitive linker peptide.

11. The vector of claim 6, where the chimeric polypeptide encoding sequence is positioned adjacent to and under the control of an effective promoter.

12. The vector of claim 11, where the promoter comprises a prokaryotic promoter, the vector being adapted for expression in a prokaryotic host.

13. The vector of claim 11, where the promoter comprises a eukaryotic promoter, the vector being adapted for expression in a eukaryotic host, and the vector further includes a polyadenylation signal position 3′ of the carboxy-terminal amino acid, and within a transcriptional unit of the encoding polypeptide.

14. The vector of claim 13, where the eukaryotic promoter comprises a cytomegalovirus promoter.

15. The recombinant host cell which incorporated an isolated DNA segment in accordance with claim 1.

16. The recombinent host cell of claim 15, further defined as a eukaryotic host cell.

17. The recombinant host cell of claim 16, further defined as a CHO cell.

18. The recombinant host cell of claim 15, further defined as a prokaryotic host cell.

19. The recombinant host cells of claim 15 where the DNA segment encoding a chimeric polypeptide is under the transcriptional control of regulatory signals functional in the recombinant host cell which regulatory signals appropriately control the expression of the chimeric polypeptide in a manner to allow all necessary transcriptional and post transcriptional modification.

20. A method of producing a chimeric polypeptide comprising the extracellular domain of the TNF receptor polypeptide functionally attached to a Fc portion and hinge region of an IgG heavy chain polypeptide, the method comprising:
(a) producing a recombinant host cell according to claim 5, such cell being capable of expressing the polypeptide;
(b) culturing the host cell under conditions appropriate for expressing the polypeptide; and
(c) recovering the chimetic polypeptide.

21. The method of claim 20, where additional steps comprise:
(a) cleaving the polypeptide at the specifically cleavable linker peptide; and
(b) recovering the polypeptide comprising an extracellular domain of the TNF receptor polypeptide.

22. The method of claim 20 wherein the host cell is a eukaryotic cell.

23. The method of claim 22 wherein the eukaryotic cell is a CHO cell.

24. The method of claim 22 wherein the eukaryotic cell is an insect cell.

25. The method of claim 20 wherein the host cell is a prokaryotic cell.

* * * * *

UNITED STATES PATENT AND TRADEMARK OFFICE
CERTIFICATE OF CORRECTION

PATENT NO. : 5,447,851
DATED : September 5, 1995
INVENTOR(S) : Bruce A. Beutler et al.

It is certified that error appears in the above-indentified patent and that said Letters Patent is hereby corrected as shown below:

Abstract, item 57, line 10, delete "polypeptides More" and insert --polypeptides. More-- therefor.

In claim 15, column 28, line 30, delete "incorporated" and insert --incorporates-- therefor.

In claim 20, column 28, line 51, delete "claim 5" and insert --claim 15-- therefor.

Signed and Sealed this

Sixteenth Day of January, 1996

Attest:

BRUCE LEHMAN

Attesting Officer     Commissioner of Patents and Trademarks

REEXAMINATION CERTIFICATE (3804th)

United States Patent [19]
Beutler et al.

[11] B1 5,447,851
[45] Certificate Issued Jul. 6, 1999

[54] DNA ENCODING A CHIMERIC POLYPEPTIDE COMPRISING THE EXTRACELLULAR DOMAIN OF TNF RECEPTOR FUSED TO IGG, VECTORS AND HOST CELLS

[75] Inventors: Bruce A. Beutler; Karsten Peppel, both of Dallas; David F. Crawford, Irving, all of Tex.

[73] Assignee: The Board of Regents of University of Texas System, Austin, Tex.

Reexamination Request:
No. 90/004,589, Mar. 25, 1997

Reexamination Certificate for:
Patent No.: 5,447,851
Issued: Sep. 5, 1995
Appl. No.: 07/862,495
Filed: Apr. 2, 1992

Certificate of Correction issued Jan. 16, 1996.

[51] Int. Cl.$^6$ .......................... C12P 21/06; C12N 15/00; C07H 17/00; C07K 14/00
[52] U.S. Cl. .................... 435/69.7; 435/69.5; 435/320.1; 435/252.3; 435/325; 536/23.4; 530/300; 530/351
[58] Field of Search ................................. 536/23.1, 23.4; 435/69.1, 69.5, 69.7, 325, 320.1; 530/350, 351, 300

[56] References Cited

U.S. PATENT DOCUMENTS 5,395,760 3/1995 Smith et al. ............................ 435/325
5,447,851 9/1995 Beutler et al. ......................... 435/69.7
5,610,279 3/1997 Brockhaus et al. .................. 530/387.3

FOREIGN PATENT DOCUMENTS

| 0 418 014 A1 | 3/1991 | European Pat. Off. . |
| 0 418 014 B1 | 3/1991 | European Pat. Off. . |
| 418014 A1 | 3/1991 | European Pat. Off. . |
| 418014 B1 | 12/1995 | European Pat. Off. . |

*Primary Examiner*—Karen Cochrane Carlson

[57] ABSTRACT

The invention relates generally to DNA sequences encoding chimeric polypeptides comprising extracellular portions of cytokine receptor polypeptides attached to a sequence encoding portions of IgG polypeptides. The invention relates generally, as well, to DNA sequences encoding chimeric polypeptides comprising extracellular portions of cytokine receptor polypeptides attached through oligomers encoding specifically cleavable peptide linkers to a sequence encoding portions of IgG heavy chain polypeptides More specifically, the invention relates to a construction in which a cDNA sequence encoding the extracellular domain of the human 55 kD TNF receptor is attached through an oligomer encoding a thrombin-sensitive peptide linker to a sequence encoding the $F_c$ portion and hinge region of a mouse IgG1 heavy chain. The invention relates as well to uses of the chimeric polypeptide, including: use as a reagent for the antagonism and assay of TNF and lymphotoxin from diverse species; use as a means of determining the mechanism by which TNF, or analogs thereof, interacts with the TNF receptor; use as an antitumor reagent, particularly against placental tumors; and, use as a reagent capable of controlling birth.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–3, 6–8 and 11–25 are cancelled.

Claims 4 and 9 are determined to be patentable as amended.

Claims 5 and 10, dependent on an amended claim, are determined to be patentable.

New claims 26–44 are added and determined to be patentable.

4. [The] *An* isolated DNA segment [of claim 1,] *having a sequence encoding a chimeric polypeptide comprising the extracellular domain of a TNF receptor polypeptide functionally attached to a Fc portion and hinge region of an IgG heavy chain polypeptide and* further incorporating a DNA segment encoding a specifically cleavable linker peptide functionally interposed between the TNF receptor polypeptide and the Fc portion.

9. [The vector of claim 6,] *A recombinant vector incorporating an isolated DNA segment having a sequence encoding a chimeric polypeptide comprising the extracellular domain of a TNF receptor polypeptide functionally attached to a Fc portion and hinge region of an IgG heavy chain polypeptide and* further incorporating a DNA segment encoding a specifically cleavable linker peptide functionally interposed between the extracellular domain of the TNF receptor polypeptide and the Fc portion.

26. *The isolated DNA segment according to claim 4, where the IgG heavy chain polypeptide is a mouse IgG polypeptide.*

27. *The isolated DNA segment according to claim 4, where the TNF receptor polypeptide is a human TNF receptor polypeptide.*

28. *The recombinant vector according to claim 9, where the IgG heavy chain polypeptide is a mouse IgG polypeptide.*

29. *The recombinant vector according to claim 9, where the TNF receptor polypeptide is a human TNF receptor polypeptide.*

30. *The recombinant vector of claim 9, where the chimeric polypeptide encoding sequence is positioned adjacent to and under the control of an effective promoter.*

31. *The recombinant vector of claim 30, where the promoter comprises a prokaryotic promoter, the vector being adapted for expression in a prokaryotic host.*

32. *The recombinant vector of claim 30, where the promoter comprises a eukaryotic promoter, the vector being adapted for expression in a eukaryotic host, and the vector further includes a polyadenylation signal positioned 3' of the carboxy-terminal codon, and within a transcriptional unit of the encoding polypeptide.*

33. *The vector of claim 32, where the eukaryotic promoter comprises a cytomegalovirus promoter.*

34. *A recombinant host cell incorporating an isolated DNA segment according to claim 4.*

35. *The recombinant host cell of claim 34, further defined as a eukaryotic host cell.*

36. *The recombinant host cell of claim 34, further defined as a CHO cell.*

37. *The recombinant host cell of claim 34, further defined as a prokaryotic host cell.*

38. *The recombinant host cell of claim 34, where the DNA segment encoding a chimeric polypeptide is under the transcriptional control of regulatory signals functional in the recombinant host cell which regulatory signals appropriately control the expression of the chimeric polypeptide in a manner to allow all necessary transcriptional and post transcriptional modification.*

39. *A method of producing a chimeric polypeptide comprising the extracellular domain of the TNF receptor polypeptide functionally attached to a Fc portion and hinge region of an IgG heavy chain polypeptide through a specifically cleavable linker peptide, the method comprising:*

(a) *producing a recombinant host cell according to claim 34, such cell being capable of expressing the chimeric polypeptide;*

(b) *culturing the host cell under conditions appropriate for expression of the chimeric polypeptide; and*

(c) *recovering the chimeric polypeptide.*

40. *The method of claim 39, further including the steps of:*

(a) *cleaving the polypeptide at the specifically cleavable linker peptide; and*

(b) *recovering the polypeptide comprising an extracellular domain of the TNF receptor polypeptide.*

41. *The method of claim 39, wherein the host cell is a eukaryotic cell.*

42. *The method of claim 41, wherein the eukaryotic cell is a CHO cell.*

43. *The method of claim 39, wherein the host cell is an insect cell.*

44. *The method of claim 39, wherein the host cell is a prokaryotic cell.*

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 6 amino acid residues
        ( B ) TYPE: amino acid
        ( C ) STRANDEDNESS: single
        ( D ) TOPOLOGY: linear ( x i ) SEQUENCE DESCRIPTION: SEQ ID NO:1:

Leu  Val  Pro  Arg  Gly  Ser
  1                    5

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

CTGGTTCCGC GTGGATCC                                                      18

( 2 ) INFORMATION FOR SEQ ID NO:3:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CTTAAGCTTA GTACTCATGT GGTGCCTGAG TCCTCAG                                 37

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

GCGCATCGAT CTGGCATGGG CCTCTCCACC                                         30

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GGATCCACGC GGAACCAGTG TGGTGCCTGA GTCCTC                                    36
```

( 2 ) INFORMATION FOR SEQ ID NO:6:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( x i ) SEQUENCE DESCRIPTION: SEQ ID NO:6:

```
CTGGTTCCGC GTGGATCCGT GCCCAGGGAT TGTGGT                                    36
```

( 2 ) INFORMATION FOR SEQ ID NO:7:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:7:

```
ATTAAGCATT CTAGATCATT TACCAGGAGA GTG                                       33
```